United States Patent [19]
Panescu et al.

[11] Patent Number: 5,810,802
[45] Date of Patent: Sep. 22, 1998

[54] SYSTEMS AND METHODS FOR CONTROLLING TISSUE ABLATION USING MULTIPLE TEMPERATURE SENSING ELEMENTS

[75] Inventors: Dorin Panescu, Sunnyvale; Sidney D. Fleischman, Menlo Park; James G. Whayne, Saratoga; David K. Swanson, Mountain View, all of Calif.

[73] Assignee: E.P. Technologies, Inc., San Jose, Calif.

[21] Appl. No.: 788,782

[22] Filed: Jan. 24, 1997

Related U.S. Application Data

[63] Continuation of Ser. No. 439,824, May 12, 1995, abandoned, which is a continuation-in-part of Ser. No. 286,930, Aug. 8, 1994, abandoned, which is a continuation-in-part of Ser. No. 287,192, Aug. 8, 1994, abandoned.

[51] Int. Cl.⁶ .................................................. A61B 17/36
[52] U.S. Cl. ............................ 606/31; 606/41; 607/101
[58] Field of Search ................... 606/27–31, 41, 606/42, 45–50; 607/100–102, 122; 600/373, 374, 549

[56] References Cited

U.S. PATENT DOCUMENTS

| | | | |
|---|---|---|---|
| 4,966,597 | 10/1990 | Cosman | 606/50 |
| 5,057,105 | 10/1991 | Malone et al. | 606/28 |
| 5,122,137 | 6/1992 | Lennox | 606/49 |
| 5,178,620 | 1/1993 | Eggers et al. | 606/41 |
| 5,334,193 | 8/1994 | Nardella | 606/41 |
| 5,406,946 | 4/1995 | Imran | 128/642 |
| 5,411,025 | 5/1995 | Webster, Jr. | 128/642 |
| 5,423,811 | 6/1995 | Imran et al. | 606/41 |
| 5,443,463 | 8/1995 | Stern et al. | 606/51 |
| 5,456,682 | 10/1995 | Edwards et al. | 606/31 |
| 5,628,771 | 5/1997 | Mizukawa et al. | 607/102 |

*Primary Examiner*—Michael Peffley
*Attorney, Agent, or Firm*—Oppenheimer Wolff & Donnelly LLP

[57] ABSTRACT

Systems and associated methods place a temperature sensing element in an "edge region" between an energy transmitting electrode and a non-electrically conducting support body, where higher temperatures are likely to exist. Reliable temperature sensing, which is sensitive to variations in temperatures along the electrode, results.

50 Claims, 16 Drawing Sheets

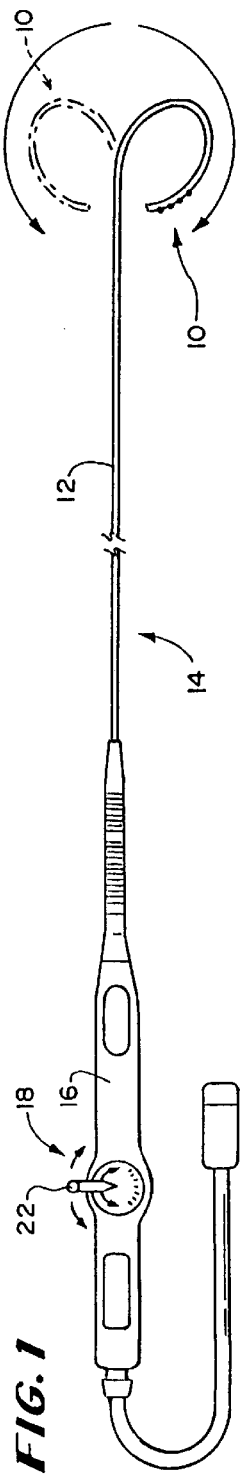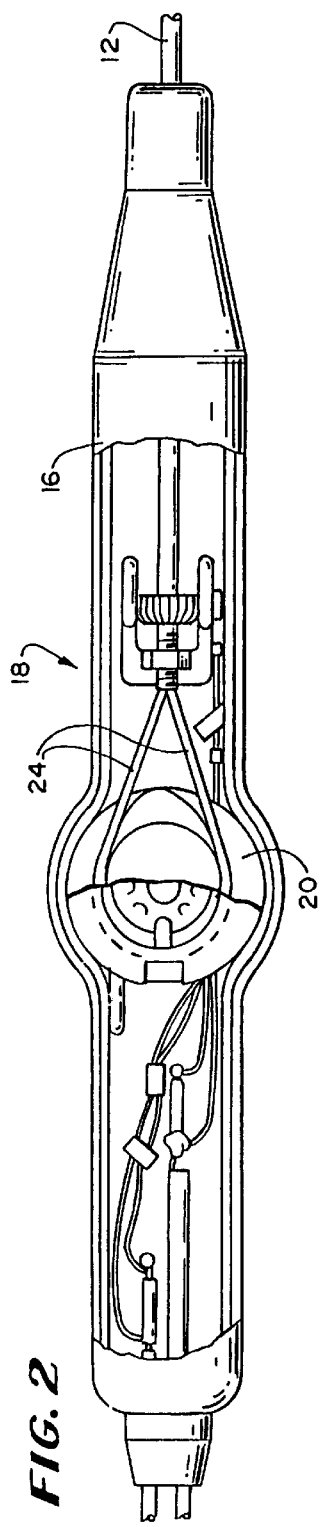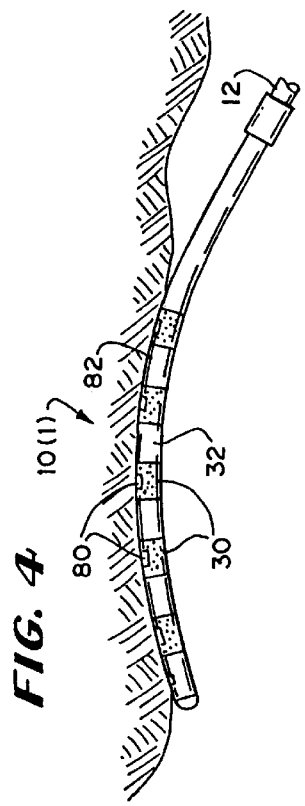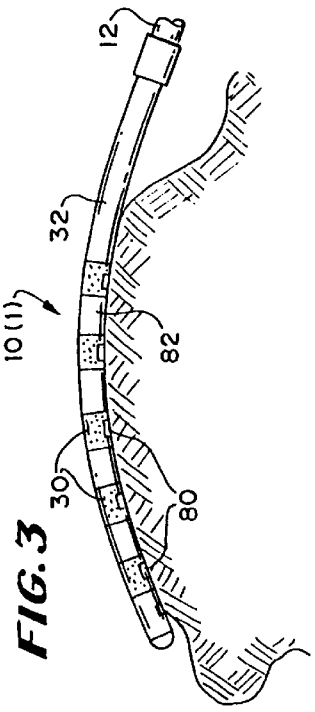
FIG. 1
FIG. 2
FIG. 3
FIG. 4

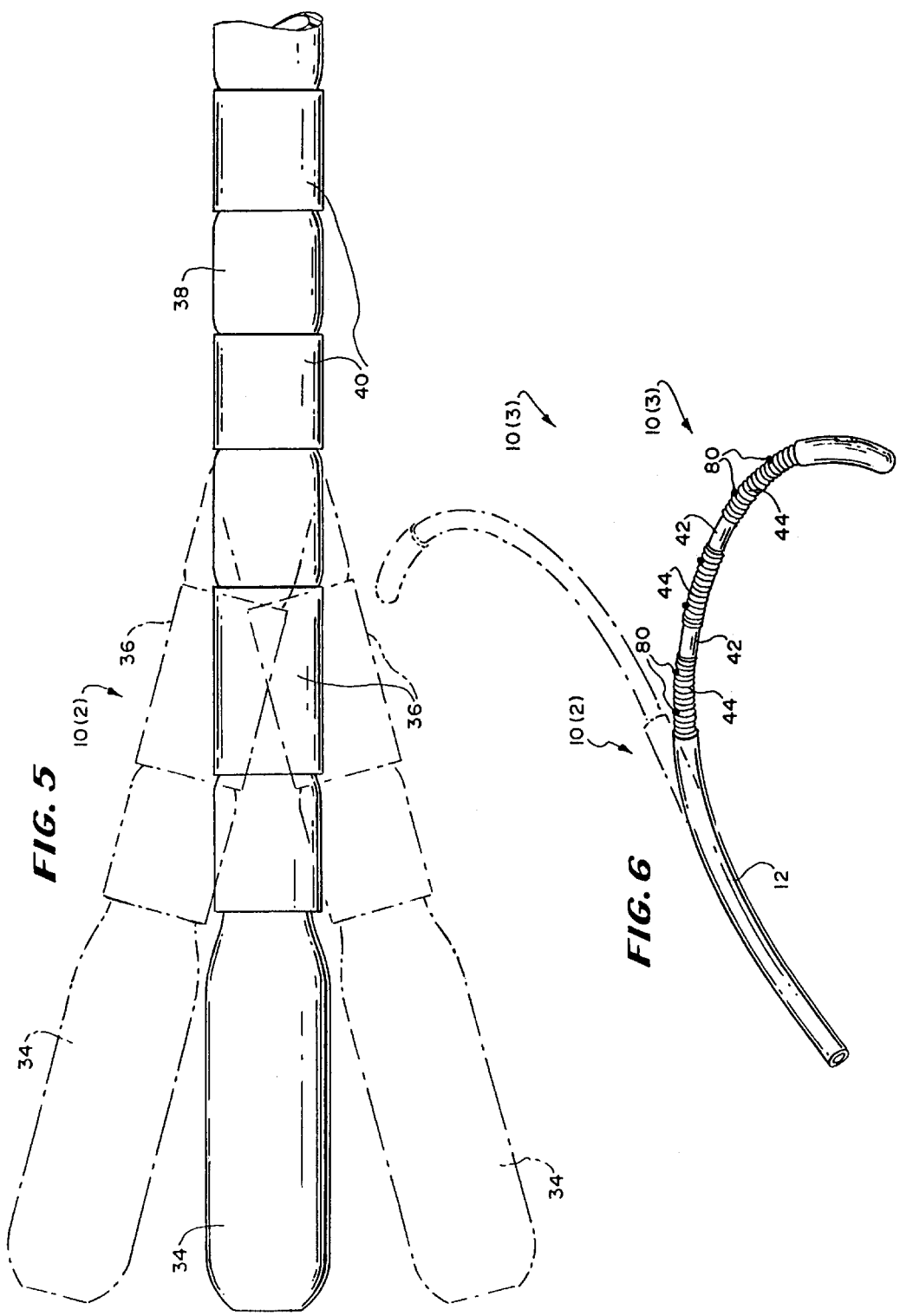

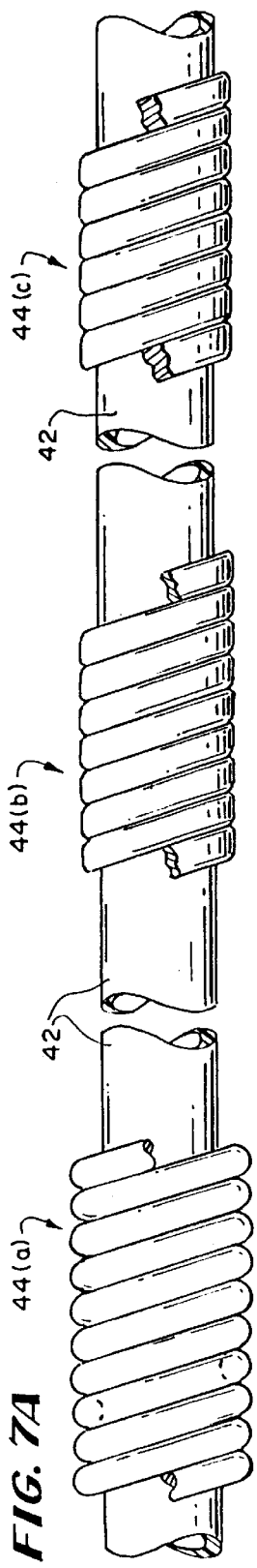
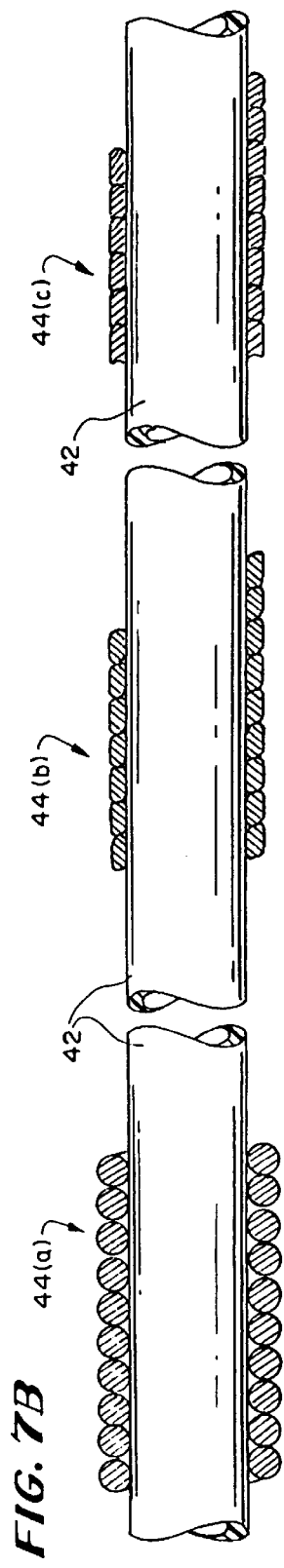
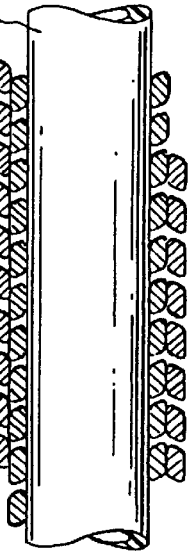

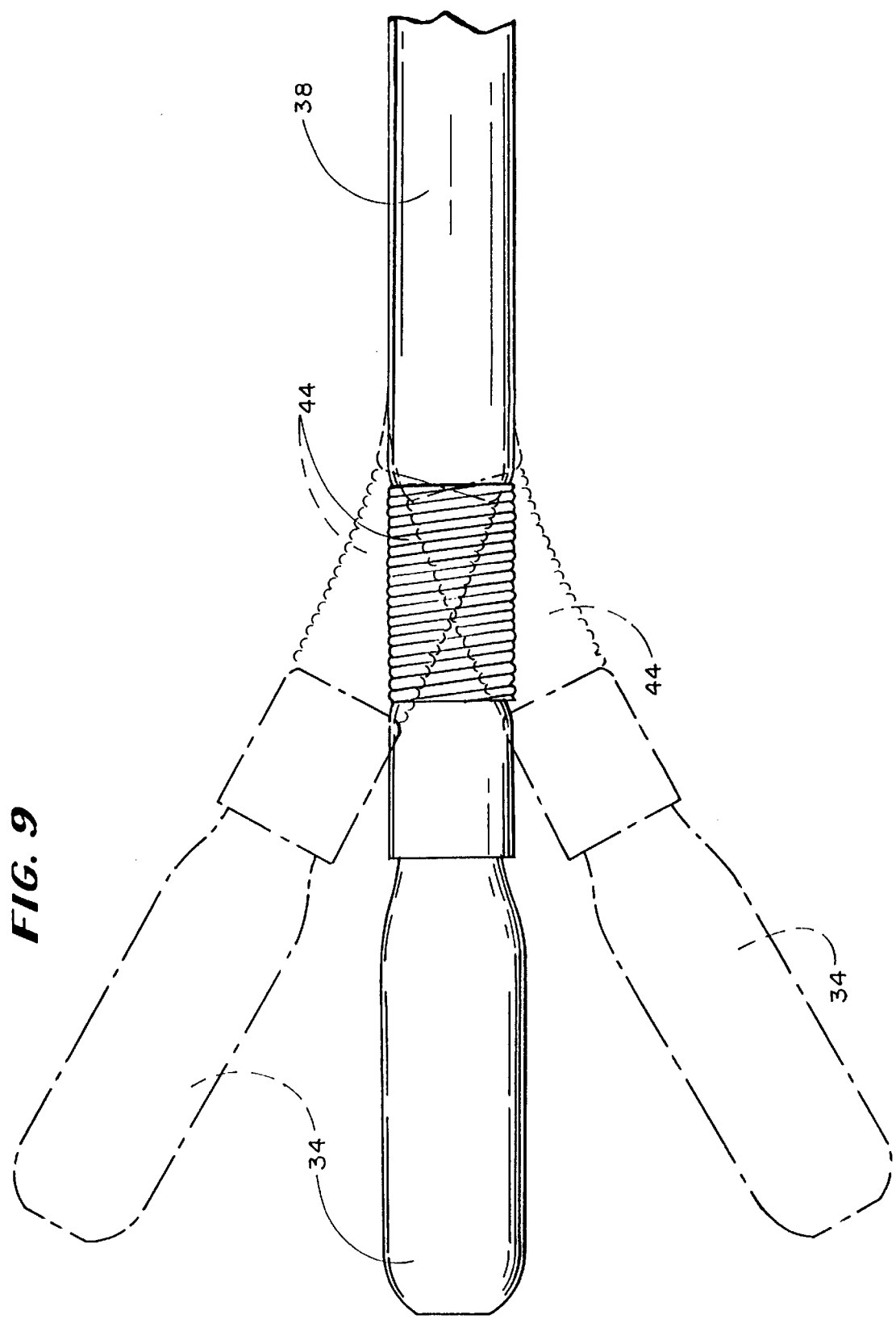

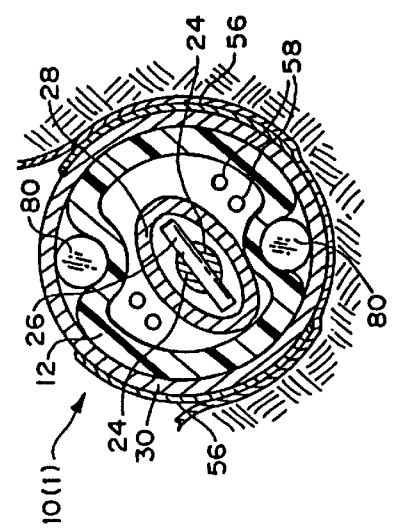
FIG. 13  FIG. 14  FIG. 15
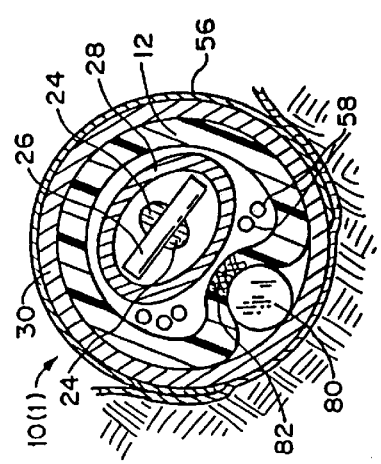
FIG. 16
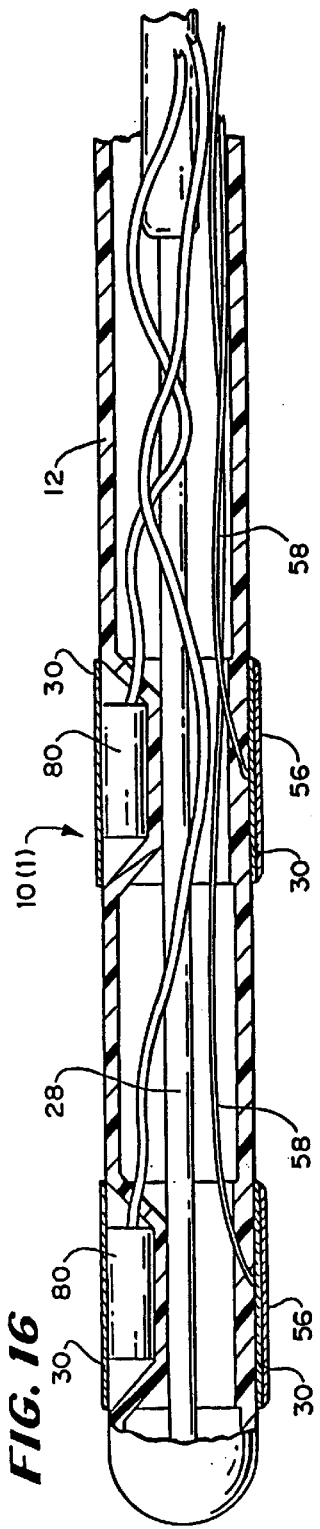

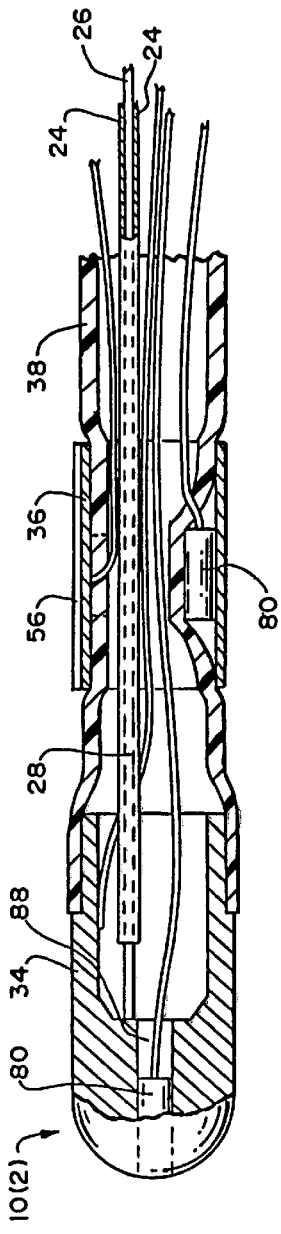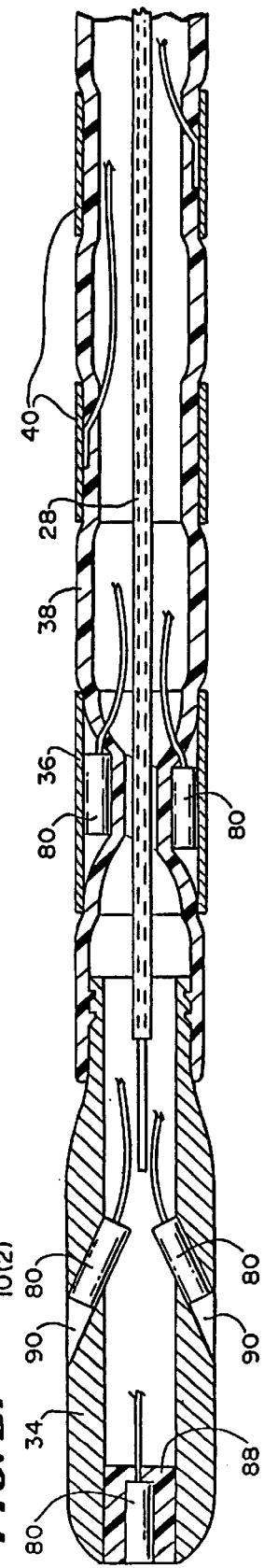
FIG. 20
FIG. 21

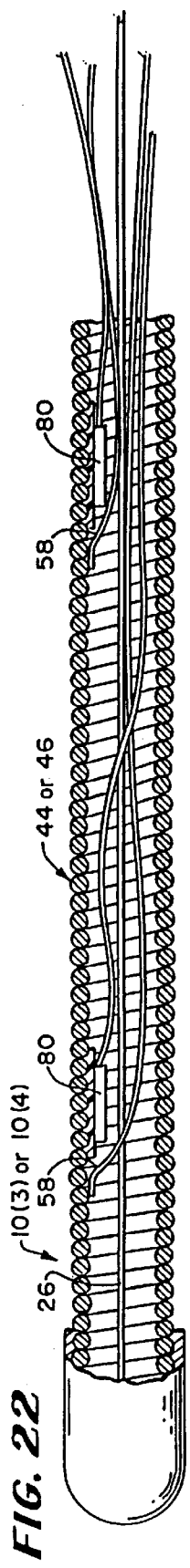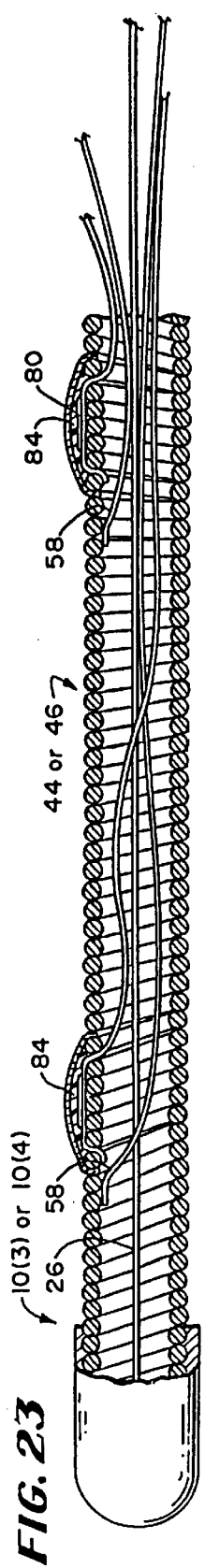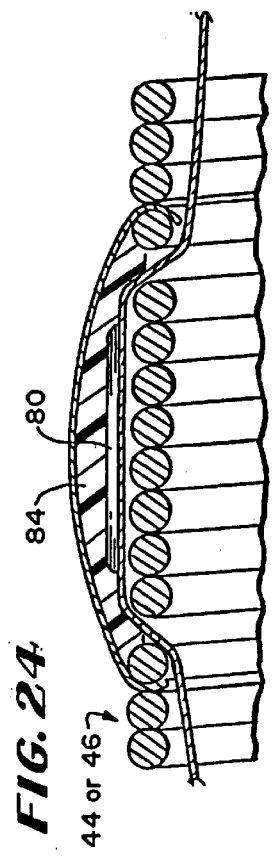

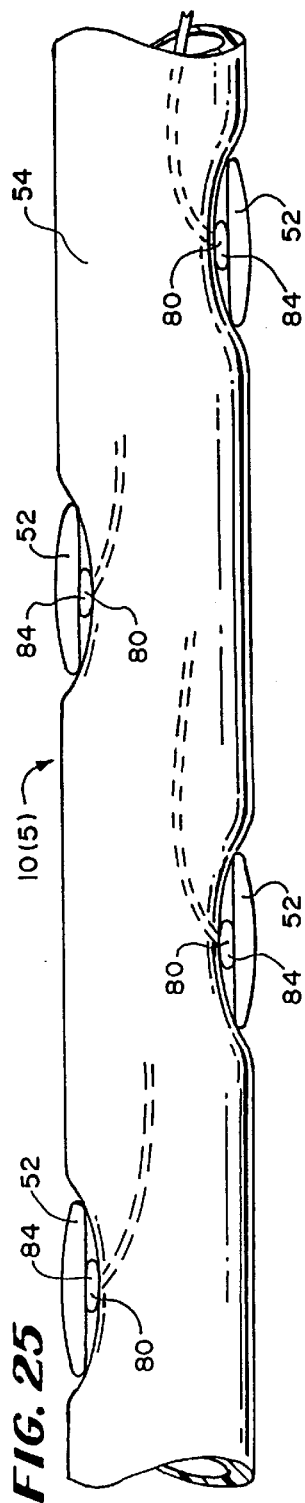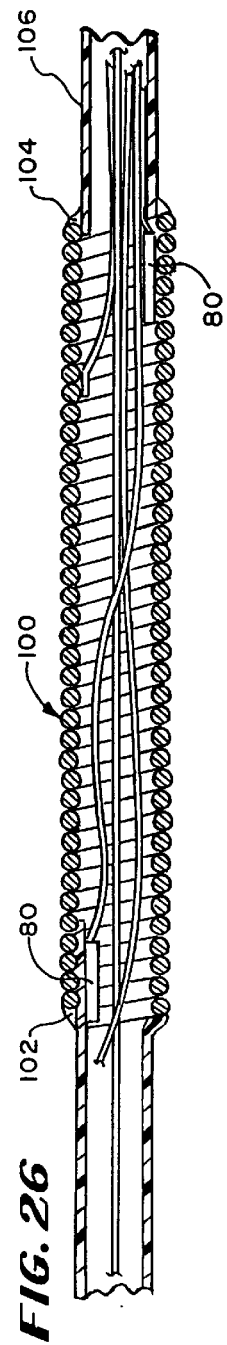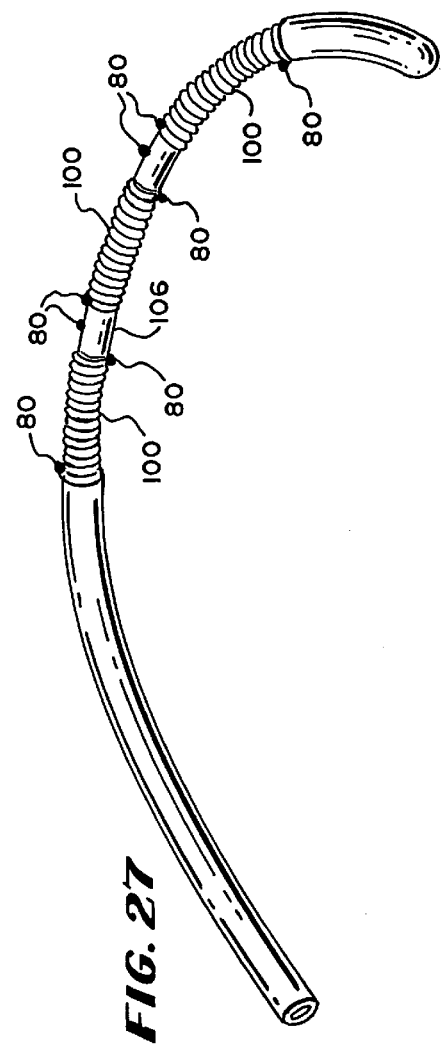
FIG. 25
FIG. 26
FIG. 27

SYSTEMS AND METHODS FOR CONTROLLING TISSUE ABLATION USING MULTIPLE TEMPERATURE SENSING ELEMENTS

RELATED CASES

This is a continuation of application Ser. No. 08/439,824 filed May 12, 1995; which is a continuation-in-part of application Ser. No. 08/286,930 filed on Aug. 8, 1994; and a continuation-in-part of application Ser. No. 08/287,192 filed Aug. 8, 1994, all now abandoned.

FIELD OF THE INVENTION

The invention relates to systems and methods for ablating myocardial tissue for the treatment of cardiac conditions.

BACKGROUND OF THE INVENTION

Physicians make use of catheters today in medical procedures to gain access into interior regions of the body to ablate targeted tissue areas. It is important for the physician to be able to precisely locate the catheter and control its emission of energy within the body during tissue ablation procedures.

For example, in electrophysiological therapy, ablation is used to treat cardiac rhythm disturbances.

During these procedures, a physician steers a catheter through a main vein or artery into the interior region of the heart that is to be treated. The physician places an ablating element carried on the catheter near the cardiac tissue that is to be ablated. The physician directs energy from the ablating element to ablate the tissue and form a lesion.

In electrophysiological therapy, there is a growing need for ablating elements capable of providing lesions in heart tissue having different geometries.

For example, it is believed the treatment of atrial fibrillation requires the formation of long, thin lesions of different curvilinear shapes in heart tissue. Such long, thin lesion patterns require the deployment within the heart of flexible ablating elements having multiple ablating regions. The formation of these lesions by ablation can provide the same therapeutic benefits that the complex suture patterns that the surgical maze procedure presently provides, but without invasive, open heart surgery.

As another example, it is believed that the treatment of atrial flutter and ventricular tachycardia requires the formation of relatively large and deep lesions patterns in heart tissue. Merely providing "bigger" electrodes does not meet this need. Catheters carrying large electrodes are difficult to introduce into the heart and difficult to deploy in intimate contact with heart tissue. However, by distributing the larger ablating mass required for these electrodes among separate, multiple electrodes spaced apart along a flexible body, these difficulties can be overcome.

With larger and/or longer multiple electrode elements comes the demand for more precise control of the ablating process. The delivery of ablating energy must be governed to avoid incidences of tissue damage and coagulum formation. The delivery of ablating energy must also be carefully controlled to assure the formation of uniform and continuous lesions, without hot spots and gaps forming in the ablated tissue.

SUMMARY OF THE INVENTION

The invention provides device and methods for ablating body tissue. The devices and methods include an electrode carried by a support element made of a material that does not conduct tissue ablation energy. The electrode is made of a material that transmits ablation energy. The electrode has at least one edge that contacts the material of the support element. The devices and methods also include at least one temperature sensing element carried by the electrode adjacent to the at least one edge.

Another aspect of the invention provides systems and methods method for controlling the ablation of body tissue. The systems and methods supply ablation energy to an electrode carried by a support element made of a material that does not conduct ablation energy. The electrode has at least one edge that contacts the material of the support element. The systems and methods senses temperature with at least one temperature sensing element carried by the electrode adjacent to the at least one edge. The systems and methods control the supply of ablation energy based, at least in part, upon temperature sensed by the at least one temperature sensing element.

The invention places the temperature sensing element in an "edge region" between an electrode and a non-electrically conducting support body. The edge region presents an area where electrical conductivity is discontinuous. The resulting rise in current density in this region generates localized increases in power densities, and, therefore, it is a region where higher temperatures are likely to exist. The invention places the temperature sensing element just where localized "hot spots" are to be expected. Reliable temperature sensing, which is sensitive to variations in temperatures along the electrode, results.

Other features and advantages of the inventions are set forth in the following Description and Drawings, as well as in the appended Claims.

BRIEF DESCRIPTION OF THE DRAWINGS

FIG. 1. is a view of a probe that carries a flexible ablating element having multiple temperature sensing elements;

FIG. 2 is an enlarged view of the handle of the probe shown in FIG. 1, with portions broken away and in section, showing the steering mechanism for flexing the ablating element;

FIGS. 3 and 4 show the flexure of the ablating element against different tissue surface contours;

FIG. 5 is a side view of a flexible ablating element comprising a rigid tip electrode element and a rigid body electrode segment;

FIG. 6 is a perspective view of a segmented flexible electrode element, in which each electrode segment comprises a wrapped wire coil;

FIGS. 7A/B are, respectively, side and side section views of different wrapped wire coils comprising flexible electrode elements;

FIGS. 8A/B are, respectively, a side and side section view of multiple wrapped wire coils comprising a flexible electrode element;

FIG. 9 is a side view of a flexible ablating element comprising a rigid tip electrode element and a flexible body electrode segment;

FIG. 13 is an end section view of an ablating electrode element carrying one temperature sensing element;

FIG. 14 is an end section view of an ablating electrode element carrying two temperature sensing elements;

FIG. 15 is an end section view of an ablating electrode element carrying three temperature sensing elements;

FIG. 16 is a side section view of a flexible ablating element comprising multiple rigid electrode elements, showing one manner of mounting at least one temperature sensing element beneath the electrode elements;

FIGS. 20 and 21 are side section views of the mounting of temperature sensing elements on the ablating element shown in FIG. 5;

FIG. 22 is a view of a flexible ablating element comprising a continuous wrapped coil, showing one manner of mounting temperature sensing elements along the length of the coil;

FIG. 23 is a view of a flexible ablating element comprising a continuous wrapped coil, showing another manner of mounting temperature sensing elements along the length of the coil;

FIG. 24 is an enlarged view of the mounting of the temperature sensing element on the coil electrode shown in FIG. 23;

FIG. 25 is a view of a flexible ablating element comprising a continuous wrapped ribbon, showing a manner of mounting temperature sensing elements along the length of the ribbon;

FIG. 26 is a side section view of a large electrode with temperature sensing elements positioned at its edges;

FIG. 27 is a perspective view of an array of long electrodes with temperature sensing elements position at each long electrode edge and in between each long electrode;

Figure 10:
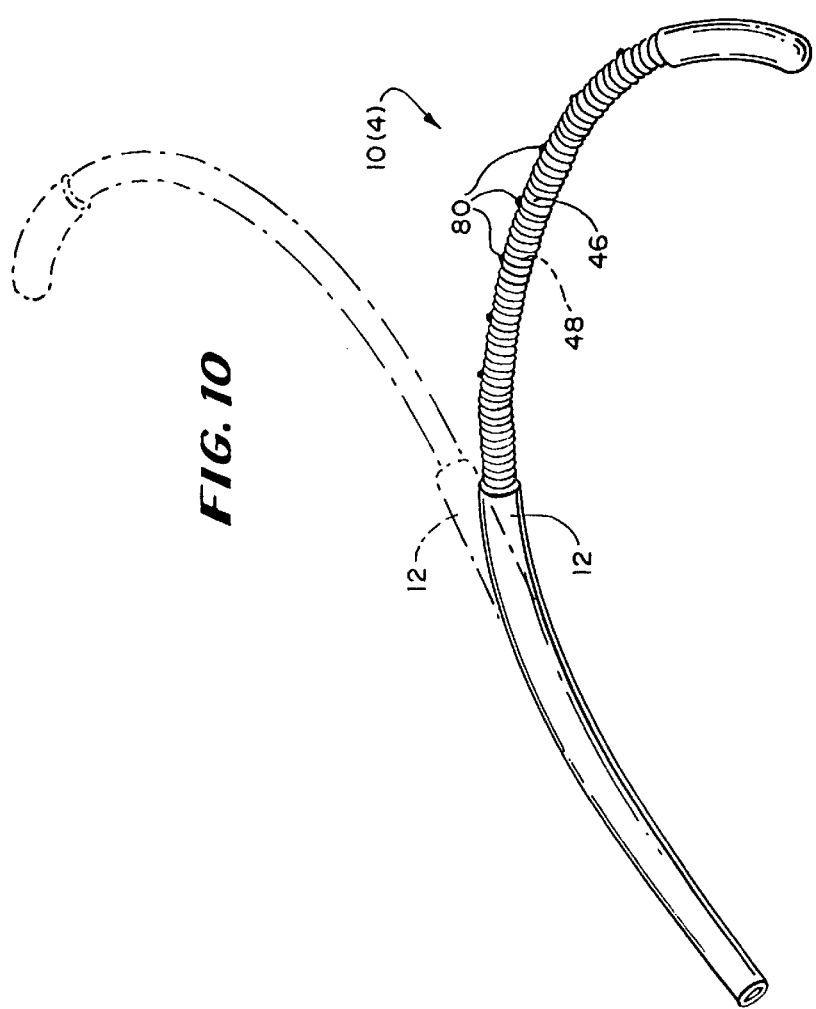
FIG. 10 is a perspective view of a continuous flexible electrode element comprising a wrapped wire coil.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

This Specification discloses multiple electrode structures that embody aspects the invention. This Specification also discloses tissue ablation systems and techniques using multiple temperature sensing elements that embody other aspects of the invention. The illustrated and preferred embodiments discuss these structures, systems, and techniques in the context of catheter-based cardiac ablation. That is because these structures, systems, and techniques are well suited for use in the field of cardiac ablation.

Still, it should be appreciated that the invention is applicable for use in other tissue ablation applications. For example, the various aspects of the invention have application in procedures for ablating tissue in the prostrate, brain, gall bladder, uterus, and other regions of the body, using systems that are not necessarily catheter-based.

I. Flexible Ablating Elements

FIG. 1 shows a flexible ablating element 10 for making lesions within the heart.

The element 10 is carried at the distal end of a catheter body 12 of an ablating probe 14. The ablating probe 14 includes a handle 16 at the proximal end of the catheter body 12. The handle 16 and catheter body 12 carry a steering mechanism 18 for selectively bending or flexing the ablating element 10 in two opposite directions, as the arrows in FIG. 1 show.

The steering mechanism 18 can vary. In the illustrated embodiment (see FIG. 2), the steering mechanism 18 includes a rotating cam wheel 20 with an external steering lever 22 (see FIG. 1). As FIG. 2 shows, the cam wheel 20 holds the proximal ends of right and left steering wires 24. The wires 24 pass through the catheter body 12 and connect to the left and right sides of a resilient bendable wire or spring 26 (best shown in FIGS. 20 and 23) enclosed within a tube 28 inside the ablating element 10.

Further details of this and other types of steering mechanisms for the ablating element 10 are shown in Lundquist and Thompson U.S. Pat. No. 5,254,088, which is incorporated into this Specification by reference.

As FIG. 1 shows, forward movement of the steering lever 22 flexes or curves the ablating element 10 down. Rearward movement of the steering lever 22 flexes or curves the ablating element 10 up.

Various access techniques can be used to introduce the probe 14 into the desired region of the heart. For example, to enter the right atrium, the physician can direct the probe 14 through a conventional vascular introducer through the femoral vein. For entry into the left atrium, the physician can direct the probe 14 through a conventional vascular introducer retrograde through the aortic and mitral valves.

Alternatively, the physician can use the delivery system shown in pending U.S. application Ser. No. 08/033,641, filed Mar. 16, 1993, and entitled "Systems and Methods Using Guide Sheaths for Introducing, Deploying, and Stabilizing Cardiac Mapping and Ablation Probes."

The physician can verify intimate contact between the element 10 and heart tissue using conventional pacing and sensing techniques. Once the physician establishes intimate contact with tissue in the desired heart region, the physician applies ablating energy to the element 10. The type of ablating energy delivered to the element 10 can vary. In the illustrated and preferred embodiment, the element 10 transmits electromagnetic radio frequency energy.

The flexible ablating element 10 can be configured in various ways. With these different configurations, the flexible ablating element can form lesions of different characteristics, from long and thin to large and deep in shape.

a. Segmented, Rigid Electrode Elements

FIGS. 3 and 4 show one implementation of a preferred type of flexible ablating element, designated 10(1). The element 10(1) includes multiple, generally rigid electrode elements 30 arranged in a spaced apart, segmented relationship upon a flexible body 32.

The flexible body 32 is made of a polymeric, electrically nonconductive material, like polyethylene or polyurethane. The body 32 carries within it the resilient bendable wire or spring with attached steering wires (best shown in FIGS. 20 and 23), so it can be flexed to assume various curvilinear shapes.

The segmented electrodes 30 comprise solid rings of conductive material, like platinum. The electrode rings 30 are pressure fitted about the body 32. The flexible portions of the body 32 between the rings 30 comprise electrically nonconductive regions.

The body 32 can be flexed between the spaced apart electrodes 30 to bring the electrode 30 into intimate contact along a curvilinear surface of the heart wall, whether the heart surface curves outward (as FIG. 3 shows) or curves inward (as FIG. 4 shows).

FIG. 5 shows an implementation of another preferred type of a flexible ablating element, of the same general style as element 10(1), designated 10(2). Element 10(2) includes two generally rigid electrode elements 34 and 36 arranged in a spaced apart relationship at the distal tip of a flexible body 38. The flexible body 38 is made of electrically insulating material, like polyurethane and PEBAX® plastic material. The body 38 carries one relatively large, rigid metal electrode 34 at its tip, which comprises a body of electrically conductive material, like platinum. The body 38 also carries another rigid electrode 36, which comprises a solid ring 36 of electrically conductive material, like platinum, pressure fitted about the body 38. As FIG. 5 shows, the ablating element 10(2) can also include one or more conventional sensing ring electrodes 40 proximally spaced from the ablating ring electrode 36. The sensing ring electrodes 40 serve to sense electrical events in heart tissue to aid the physician in locating the appropriate ablation site.

As shown in phantom lines in FIG. 5, the flexible body 38, when pressed against the endocardial surface targeted for ablation, bends to place the sides of the rigid electrodes 34 and 36 in intimate contact against the particular contour of the surface. The flexible nature of the ablating element 10(2) can be further augmented by the inclusion of the resilient bendable wire or spring 26 within it (best shown in FIG. 20). In this embodiment, the steering wires 24 connect to the left and right sides of the bendable wire 26. The opposite ends of the steering wires 24 connect to a steering mechanism of the type previously described and shown in FIG. 2. In this arrangement, the physician can use the steering mechanism to remotely flex the electrodes 34 and 36 in the manner shown in FIG. 5.

Preferably, as FIG. 20 shows, the steering wires 24 are secured to the bendable wire 26 near its distal end, where the bendable wire 26 is itself secured to the tip electrode 34.

Bending of the wire 26 thereby directly translates into significant relative flexing of the distal end of the catheter body 38, which carries the electrodes 34 and 36.

Alternatively, the region between the electrodes 34 and 36 can be stiff, not flexible. In this arrangement, pressing the 34 and 36 against tissue brings the tissue into conformance about the electrodes 34 and 36.

The generally rigid, segmented electrodes 30 in element 10(1) and 34/36 in element 10(2) can be operated, at the physician's choice, either in a unipolar ablation mode or in a bipolar mode. In the unipolar mode, ablating energy is emitted between one or more the electrodes 30 (in element 10(1)) or electrodes 34/36 (in element 10(2)) and an external indifferent electrode. In the bipolar mode, ablating energy is emitted between two of the electrodes 30 (in element 10(1)) or the electrodes 34 and 36 (in element 10(2)), requiring no external indifferent electrode.

B. Flexible Electrode Elements

FIG. 6 shows an implementation of another preferred style of a flexible ablating element, designated 10(3). The element 10(3), unlike elements 10(1) and 10(2), includes generally flexible electrode elements 44 carried on a likewise flexible body 42.

Figure 29:
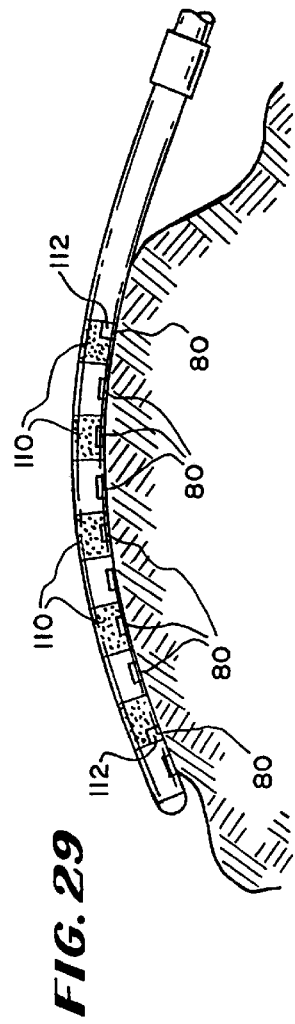
FIG. 29 is a side view of an array of short electrodes, with temperature sensing elements position at the edge of the short electrodes beginning and ending the array, as well as in the middle of each intermediate short electrode.

The flexible body 42 is made of a polymeric, electrically nonconductive material, like polyethylene or polyurethane, as the flexible body of elements 10(1) and 10(2). The body 42 also preferably carries within it the resilient bendable wire or spring 26 with attached steering wires 24 (best shown in FIGS. 29 and 30), so it can be flexed to assumed various curvilinear shapes, as FIG. 6 shows.

The body 32 carries on its exterior surface an array of segmented, generally flexible electrodes 44 comprising spaced apart lengths of closely wound, spiral coils. The coil electrodes 44 are made of electrically conducting material, like copper alloy, platinum, or stainless steel. The electrically conducting material of the coil electrode 44 can be further coated with platinum-iridium or gold to improve its conduction properties and biocompatibility.

The coils 44 can be made of generally cylindrical wire, as the coil 44(a) shown in FIGS. 7A/B. Alternatively, the wire forming the coils 44 can be non-circular in cross section. The wire, for example, have a polygon or rectangular shape, as the coil 44(b) shown in FIGS. 7A/B. The wire can also have a configuration in which adjacent turns of the coil nest together, as the coil 44(c) shown in FIGS. 7A/B. Coils 44(b) and 44(c) in FIGS. 7A/B present a virtually planar tissue-contacting surface, which emulates the tissue surface contact of the generally rigid electrode 30 shown in FIGS. 3 and 4. However, unlike the electrode 30, the coils 44(b) and 44(c), as well as the cylindrical coil 44(a), are each inherently flexible and thereby better able to conform to the surface contour of the tissue.

In another alternative arrangement, each coil 44 can comprise multiple, counter wound layers of wire, as the coil 44(d) shown in FIGS. 8A/B. This enhances the energy emitting capacity of the coil 44(d), without significantly detracting from its inherent flexible nature. The multiple layer coil 44(d) structure can also be formed by using a braided wire material (not shown).

An alternative arrangement (shown in FIG. 9) uses the generally rigid tip electrode 34 (like that in element 10(2), shown in FIG. 5) in combination with a generally flexible electrode segment 44 made of a closely wound coil. Of course, the tip electrode 34, too, could comprise a generally flexible electrode structure made of a closely wound coil. It should be apparent by now that many combinations of rigid and flexible electrode structures can be used in creating a flexible ablating element.

Furthermore, the inherent flexible nature of a coiled electrode structures 44 makes possible the construction of a flexible ablating element (designated 10(4) in FIG. 10) comprising a continuous elongated flexible electrode 46 carried by a flexible body 48. The continuous flexible electrode 46 comprises an elongated, closely wound, spiral coil of electrically conducting material, like copper alloy, platinum, or stainless steel, wrapped about the flexible body. For better adherence, an undercoating of nickel or titanium can be applied to the underlying flexible body. The continuous coil electrode 46 can be arranged and configured in the same fashion as the segmented coil electrodes 44 shown in FIGS. 7A/B and 8A/B.

The continuous coil electrode 46 is flexible and flexes with the underlying body 48, as FIG. 10 shows. It can be easily placed and maintained in intimate contact against heart tissue. The continuous flexible coil structure shown in FIG. 10 therefore makes possible a longer, flexible ablating element.

In an alternative arrangement (shown in FIGS. 12A/B), the elongated coil electrode 46 can include a sliding sheath 50 made of an electrically nonconducting material, like polyamide. a stylet (not shown) attached to the sheath 50 extends through the associated catheter body 12 to a sliding control lever carried on the probe handle 16 (also not shown). Moving the sheath 50 varies the impedance of the coil electrode 46. It also changes the surface area of the element 10(4).

Further details of this embodiment can be found in copending U.S. patent application Ser. No. 08/137,576, filed Oct. 15, 1993, and entitled "Helically Wound Radio Frequency Emitting Electrodes for Creating Lesions in Body Tissue," which is incorporated into this Specification by reference.

Figure 11:
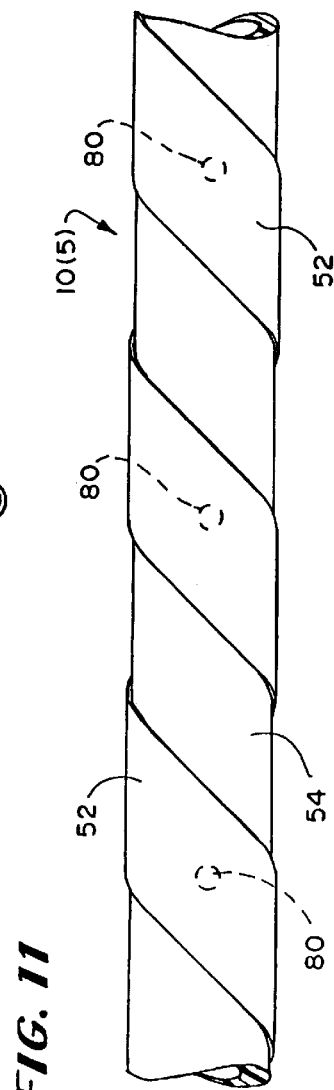
FIG. 11 is a perspective view of a continuous flexible electrode element comprising a wrapped ribbon.

FIG. 11 shows another implementation of a generally flexible element, designated element 10(5). The element 10(5) comprises a ribbon 52 of electrically conductive material wrapped about a flexible body 54. The ribbon 52 forms a continuous, inherently flexible electrode element.

Alternatively, the flexible electrodes can be applied on the flexible body by coating the body with a conductive material, like platinum-iridium or gold, using conventional coating techniques or an ion beam assisted deposition (IBAD) process. For better adherence, an undercoating of nickel or titanium can be applied. The electrode coating can be applied either as discrete, closely spaced segments (to create an element like 10(3)) or in a single elongated section (to create an element like 10(4) or 10(5)).

The flexible electrodes of elements 10(1) to 10(5) can be operated, at the physician's choice, either in a unipolar ablation mode or in a bipolar mode.

The ablating elements 10(1) to 10(5), as described above, are infinitely versatile in meeting diverse tissue ablation criteria.

For example, the ablating elements 10(1) and 10(3) to 10(5) can be conditioned to form different configurations of elongated (i.e., generally long and thin) lesion patterns. These elongated lesion patterns can be continuous and extend along a straight line or along a curve. Alternatively, these elongated lesion patterns can be segmented, or interrupted, and extend along a straight line or along a curve. Elongated lesion patterns can be used to treat, for example, atrial fibrillation.

Alternatively, the ablating elements 10(1) to 10(5) can be conditioned to form larger and deeper lesions in the heart. These lesion large and deep lesion patterns can be used to treat, for example, atrial flutter or ventricular tachycardia.

Various ways to control the characteristics of lesions formed by the ablating elements 10(1) to 10(5) are disclosed in detail in U.S. application Ser. No. 08/287,192, filed Aug. 8, 1994, entitled "Systems and Methods for Forming Elongated Lesion Patterns in Body Tissue Using Straight or Curvilinear Electrode Elements."

II. Temperature Sensing

In the illustrated and preferred embodiments, each flexible ablating element 10(1) to 10(5) carries at least one and, preferably, at least two, temperature sensing element 80. The multiple temperature sensing elements 80 measure temperatures along the length of the element 10.

a. Temperature Sensing with Rigid Electrode Elements

In the segmented element 10(1) (see FIGS. 3 and 4), each electrode segment 30 preferably carries at least one temperature sensing element 80. In this configuration, the sensing elements 80 are preferably located in an aligned relationship along one side of each segmented electrode 30, as FIGS. 3 and 4 show.

The body 32 preferably carries a fluoroscopic marker (like the stripe 82 shown in FIGS. 3 and 4) for orientation purposes. The stripe 82 can be made of a material, like tungsten or barium sulfate, which is extruded into the tubing 12. The extruded stripe can be fully enclosed by the tubing or it can be extruded on the outer diameter of the tubing making it visible to the eye. FIG. 5 shows the marker in the wall of the tubing 12. An alternative embodiment can be a fluoro-opaque wire like platinum or gold which can be extruded into the tubing wall. Yet another embodiment is to affix a marker in the inner diameter of the tubing during manufacturing.

The sensing elements 80 can be on the same side as the fluoroscopic marker 82 (as FIGS. 3 and 4 show), or on the opposite side, as long as the physician is aware of the relative position of them. Aided by the marker 82, the physician orients the element 10(1) so that the temperature sensing elements 80 contact the targeted tissue.

Alternatively, or in combination with the fluoroscopic marker 82, the sensing elements 80 can be consistently located on the inside or outside surface of element 10(1) when flexed in a given direction, up or down. For example, as FIG. 3 shows, when the element 10(1) is flexed to the down, the sensing elements 80 are exposed on the inside surface of the element 10(1). As FIG. 4 shows, when the element 10(1) flexed to the upward, the sensing elements 80 are exposed on the outside surface of the element 10 (1).

Each electrode segment 30 can carry more than a single temperature sensing element 80. As FIGS. 13 to 15 show, each electrode segment 30 can carry one, two, three, or more circumferentially spaced apart temperature sensing elements 80. The presence of multiple temperature sensing elements 80 on a single electrode segment 30 gives the physician greater latitude in positioning the ablating element 10(1), while still providing temperature monitoring.

As FIG. 13 shows, a mask coating 56 of an electrically and thermally insulating material can also be applied to the side of the single sensor-segmented electrode 30 opposite to the temperature sensing element 80, which, in use, is exposed to the blood pool. As FIG. 14 shows, the mask coating 56 lies between the two sensors 80 on the bi-directional segmented electrode 30. The mask coating 56 minimizes the convective cooling effects of the blood pool upon the regions of the electrode segment 80 that are exposed to it. The temperature condition sensed by the element 80 facing tissue is thereby more accurate. When more than two temperature sensors 80 are used on a given electrode segment 30, masking becomes less advisable, as it reduces the effective surface of the electrode segment 30 available for tissue contact and ablation.

The temperature sensing elements 80 can comprise thermistors or thermocouples. When using thermocouples as the sensing elements 80, a reference or cold junction thermocouple must be employed, which is exposed to a known temperature condition. The reference thermocouple can be placed within the temperature processing element itself. Alternatively, the reference thermocouple can be placed within the handle 18 of the catheter probe 14.

Further details regarding the use of thermocouples can be found in a publication available from omega, entitled *Temperature*, pages T-7 to T-18. Furthermore, details of the use of multiple thermocouples as temperature sensing elements 80 in tissue ablation can be found in copending patent application Ser. No. 08/286,937, filed Aug. 8, 1994, entitled "Systems and Methods for Sensing Temperature Within the Body."

The sensing element or elements 80 can be attached on or near the segmented electrodes 30 in various way.

For example, as FIG. 16 shows for the element 10(1), each sensing element 80 is sandwiched between the exterior of the flexible body 32 and the underside of the associated rigid electrode segment 30. In the illustrated embodiment, the sensing elements 80 comprise thermistors. The body 32 is flexible enough to fit the sensing element 80 beneath the electrode segment 30. The plastic memory of the body 32 maintains sufficient pressure against the temperature sensing element 80 to establish good thermal conductive contact between it and the electrode segment 30.

Figure 17:
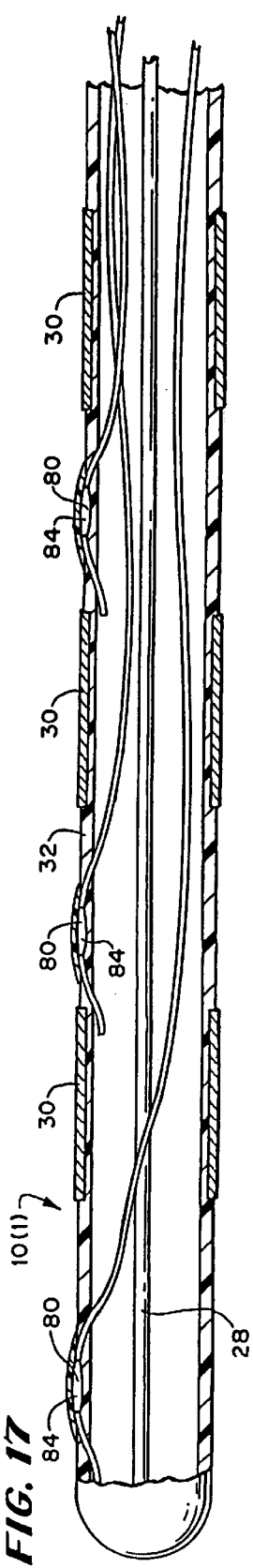
FIG. 17 is a side section view of a flexible ablating element comprising multiple rigid electrode elements, showing another manner of mounting at least one temperature sensing element between adjacent electrode elements.

In an alternative embodiment (as FIG. 17 shows), the temperature sensing element 80 is located between adjacent electrode segments 30. In this arrangement, each sensing element 80 is threaded through the flexible body 32 between adjacent electrode segments 30. In the illustrated embodiment, the temperature sensing elements 80 comprise thermocouples. When the sensing element 80 comprises a thermocouple, an epoxy material 46, such as Master Bond Polymer System EP32HT (Master Bond Inc., Hackensack, N.J.), encapsulates the thermocouple junction 84, securing it to the flexible body 32. Alternatively, the thermocouple junction 84 can be coated in a thin layer of polytetrafluoroethylene (PTFE) material. When used in thicknesses of less than about 0.002 inch, these materials have the sufficient insulating properties to electrically insulate the thermocouple junction 84 from the associated electrode segment 30, while providing sufficient thermally conducting properties to establish thermal conductive contact with electrode segment 30. The use of such materials typically will not be necessary when thermistors are used, because conventional thermistors are already encapsulated in an electrically insulating and thermally conducting material.

Figure 18:
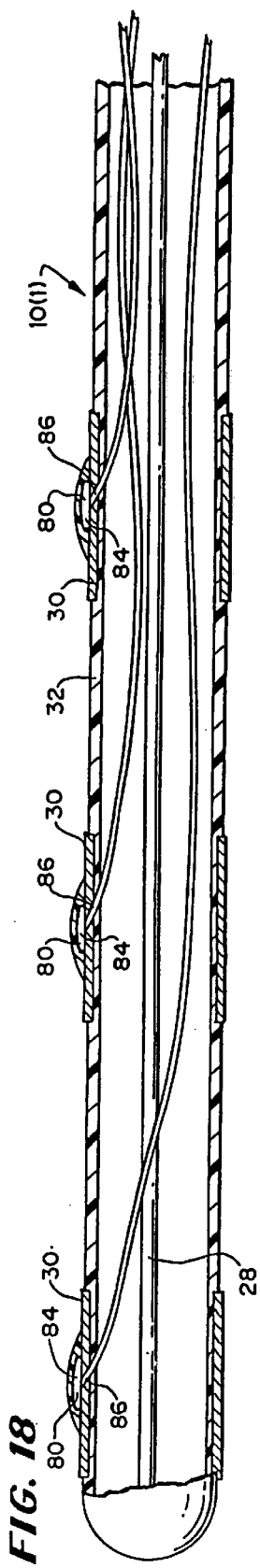
FIG. 18 is a side section view of a flexible ablating element comprising multiple rigid ablating elements, showing another manner of mounting at least one temperature sensing element on the electrode elements.
Figure 19:
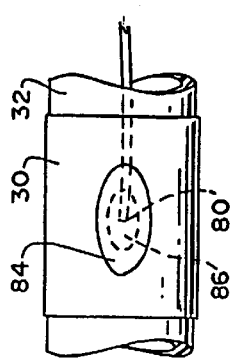
FIG. 19 is an enlarged top view of the mounting the temperature sensing element on the rigid electrode shown in FIG. 18.

In another alternative embodiment (as FIGS. 18 and 19 show), the temperature sensing element 80 physically projects through an opening 86 in each electrode segment 30. As in the embodiment shown in FIG. 17, the sensing elements 80 comprise thermocouples, and a thermally conducting and electrically insulating epoxy material encapsulates the thermocouple junction 84, securing it within the opening 86.

It should be appreciated that some sensing elements 80 can be carried by the electrode segments 30, while other sensing elements 80 can be carried between the element segments 30. Many combinations of sensing element locations are possible, depending upon particular requirements of the ablating procedure.

In the element 10(2) (see FIG. 20), each electrode segment 34 and 36 carries at least one temperature sensing element 80. In the illustrated embodiment, the sensing element 80 comprises a thermistor.

The tip electrode segment 34 carries a temperature sensing element 80 within a cavity 88 drilled along its axis. The body electrode segment 36 also carries at least one temperature sensing element 80, which is sandwiched beneath the electrode segment 36 and the flexible body 38, in the manner previously described and shown in FIG. 16. The sensing element 80 in the electrode segment 36 can be alternatively secured in the manners previously described and shown in FIGS. 17 and 18. Alternatively, as earlier described, the side of the electrode segment 36 opposite to the single sensing temperature element 80 can carrying the mask coating 56.

As shown in FIG. 21, either or both electrodes 34 and 36 of element 10(2) can carry more than one temperature sensing element 80. In this arrangement, the tip electrode 34 carries additional temperature sensing elements 80 in side cavities 90 that extend at angles radially from the axis of the electrode 34. The body electrode segment 36 carries additional sensing elements 80 in the manner shown in FIGS. 14 and 15.

As the diameter of the electrodes 34 and 36 increases, the use of multiple temperature sensing elements 80 becomes more preferred. The multiple sensing elements 80 are circumferentially spaced to assure that at least one element 80 is in thermal conductive contact with the same tissue area as the associated electrode 34 or 36.

B. Temperature Sensing with Flexible Electrode Elements

In the flexible electrode elements 10(3) and 10(4) (earlier shown in FIGS. 6 and 10), the multiple temperature sensing elements 80 are preferably located at or near the electrical connection points between the wires 58 and the coil electrode segments 44 or continuous coil electrode 46, as FIGS. 22 and 23 best show. This location for the temperature sensing elements 80 is preferred because higher temperatures are typically encountered at these connection points along the coil electrode 44 or 46.

As FIG. 22 shows, the sensing elements 80 can be secured to the inside surface of the coil electrode 44 or 46. Alternatively, the sensing elements 80 can be sandwiched between the inside surface of the electrode 44 or 46 and an underlying flexible body, as FIGS. 15A/B show. In FIGS. 15A/B and 29, the sensing elements 80 comprise thermistors.

Alternatively, as FIGS. 23 and 24 show, the sensing elements 80 can be threaded up through the windings in the coil electrode 44 or 46 to lay upon its exterior surface. In the illustrated embodiment, the sensing elements 80 comprise thermocouples, and the thermocouple junction 84 is encapsulated in on an epoxy or PTFE coating, as previously described.

Figure 12A:
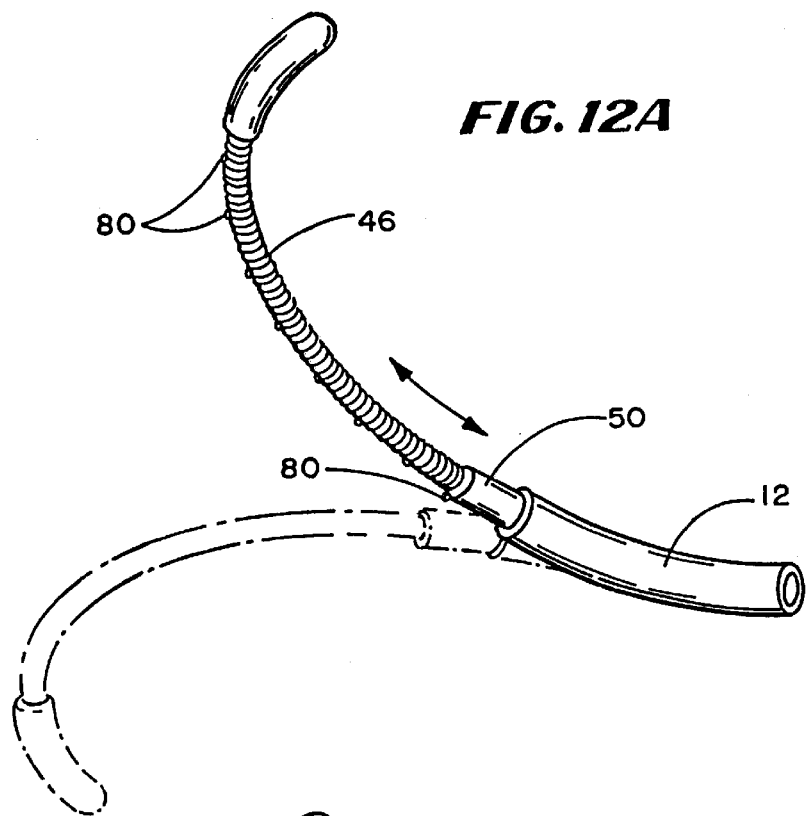
FIGS. 12A/B are views of a flexible ablating element comprising a wrapped wire coil including a movable sheath for changing the impedance of the coil and the ablating surface area when in use.
Figure 12B:
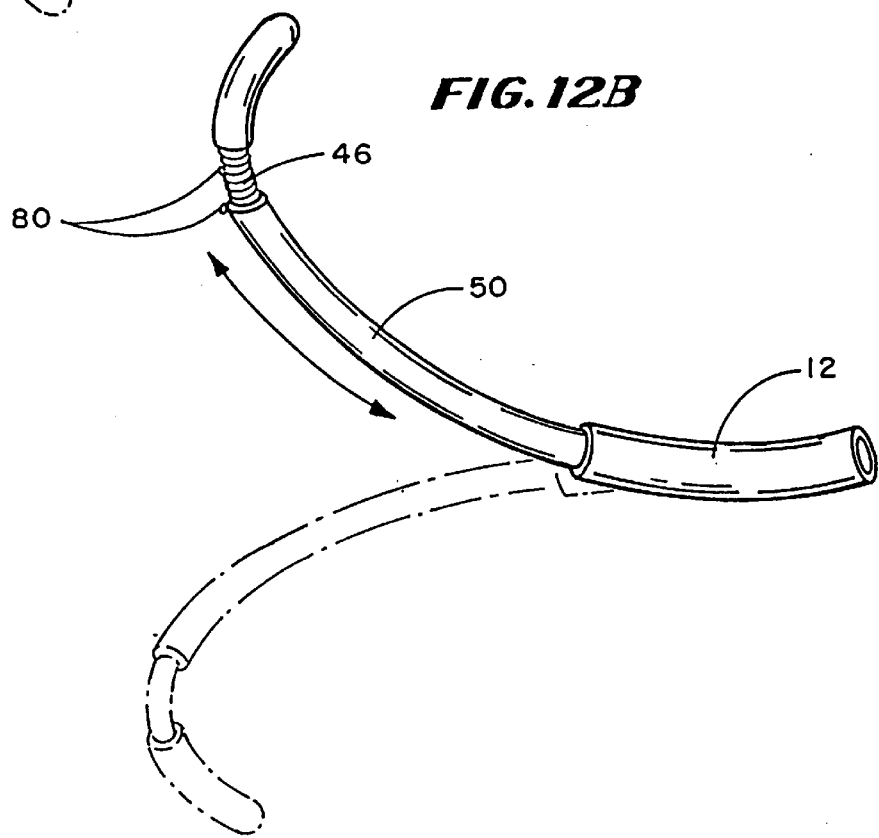

When the elongated electrode 46 includes a sliding sheath 50 see FIGS. 12A/B), the movable sheath 50 carries, in addition to the temperature sensing elements 80 spaced along the length of the coil electrode 56, another temperature sensing element 80 at its distal end.

In the case of flexible electrode element 10(5) (earlier shown in FIG. 11), the sensing elements 80 are sandwiched between the wrapped ribbon 52 and the underlying flexible body 54, as FIG. 25 shows. In the illustrated embodiment, the sensing elements 80 comprise thermocouples having junctions 84 encapsulated in an electrically insulating and thermally conducting coating.

C. Location of Temperature Sensing Elements

The positioning of the temperature sensing elements 80 on the electrode elements is important for achieving reliable temperature sensing, particularly when the length of an individual electrode on the element 80 exceeds about 10 mm, or when the element 10 comprises arrays of shorter, segmented electrodes. Without proper placement of the temperature sensor elements 80 under these circumstances, variations in tissue temperature, and in particular the presence of "hot spots," can go undetected. Also, with predetermined placement of the temperature sensing elements, temperature gradients along the element 10 can be obtained for ablation control purposes.

Electrode elements having lengths exceeding about 10 mm will be called "long" electrodes, which is identified by the numeral 100 in FIG. 26. The elongated coil electrode 46 shown in FIG. 10 exemplifies a typical long electrode. FIGS. 6 and 9 also show an arrangement in which each coil electrode segment 44 could comprise a long electrode.

As FIG. 26 shows, in a preferred embodiment, the temperature sensing elements 80 are preferably located at the edges 102 and 104 of the long electrode 100. The edges 102 and 104 are where the electrode 100 abuts the underlying, non-electrically-conductive support body 106. RF current densities are high at these edges 102 and 104, because the edges 102 and 104 are regions where electrical conductivity is discontinuous. The resulting rise in current density at the electrode edges 102 and 104 generates localized regions of increased power density and, therefore, regions where higher temperatures exist. In long electrode elements 100, temperature sensing elements 80 should preferably be located in these edge regions where high localized temperatures are to be expected.

Most preferably, as FIG. 26 shows, two temperature sensing elements 80 should be located on each long electrode 100, with the temperature sensing elements 80 positioned in oppositely spaced relationship on each edge 102 and 104 of the long electrode 100.

When sequences of long electrodes 100 are used (see FIG. 27), an additional temperature sensing element 80 should also preferably be located in between adjacent long electrodes 100. When positioned in this way, the temperature sensing elements 80 can acquire temperature gradients along the entire electrode element 10, which can be used to control the application of ablation energy, as will be described later.

The use of multiple temperature sensing elements 80 on opposite sides of long electrode 100 also reduces the sensitivity of temperature control to poor electrode contact with tissue, and also reduces errors should one or more temperature sensing elements face blood instead of tissue. This is because the probability of at least one sensor facing the tissue is increased.

Figure 28:
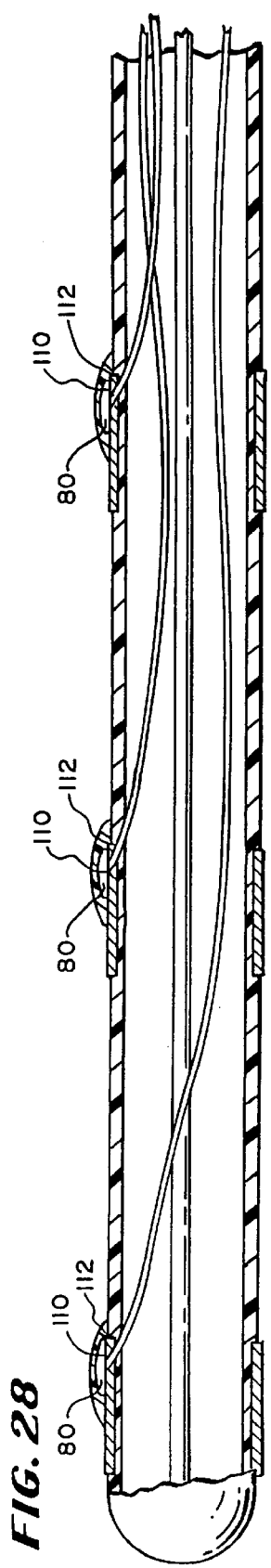
FIG. 28 is a side section view of an array of short electrodes, each one carrying a temperature sensing element at one edge.

Electrode elements having lengths less than about 10 mm will be called "short" electrodes, which are identified by the numeral 110 in FIG. 28. The segmented electrodes 30 shown in FIG. 3 exemplify a typical sequence of short electrodes. FIGS. 6 and 9 also show an arrangement in which each coil electrode segment 44 could comprise a short electrode.

When sequences of short electrodes 110 are used (see FIG. 28), the temperature sensing elements 80 are also preferable located at one edge 112 of each short electrode 110, for the same reasons explained above in connection with long electrodes 100. Still, when the electrodes 110 are very short (for example, less than about 5 mm)(see FIG. 29), a centrally located temperature sensing element 80 can be used (as FIGS. 3 and 18 also show, for example). In this arrangement (see FIG. 29), the short electrodes 110 that begin and end the electrode sequence should preferably carry temperature sensing elements 80 located at their edges 112. In such an arrangement (as FIG. 29 also shows), it is also preferable to locate additional temperature sensing elements 80 generally midway between adjacent short electrodes 110. The temperature sensing elements 80 are thereby positioned to obtain temperature gradients along the entire length of the electrode element 10.

III. Control of Cardiac Ablation Using Multiple Temperature Feedback Control FIG. 30 shows, in schematic form, a representative system 200 for applying ablating energy by multiple emitters based, at least in part, upon local temperature conditions sensed by multiple sensing elements 80.

Figure 30:
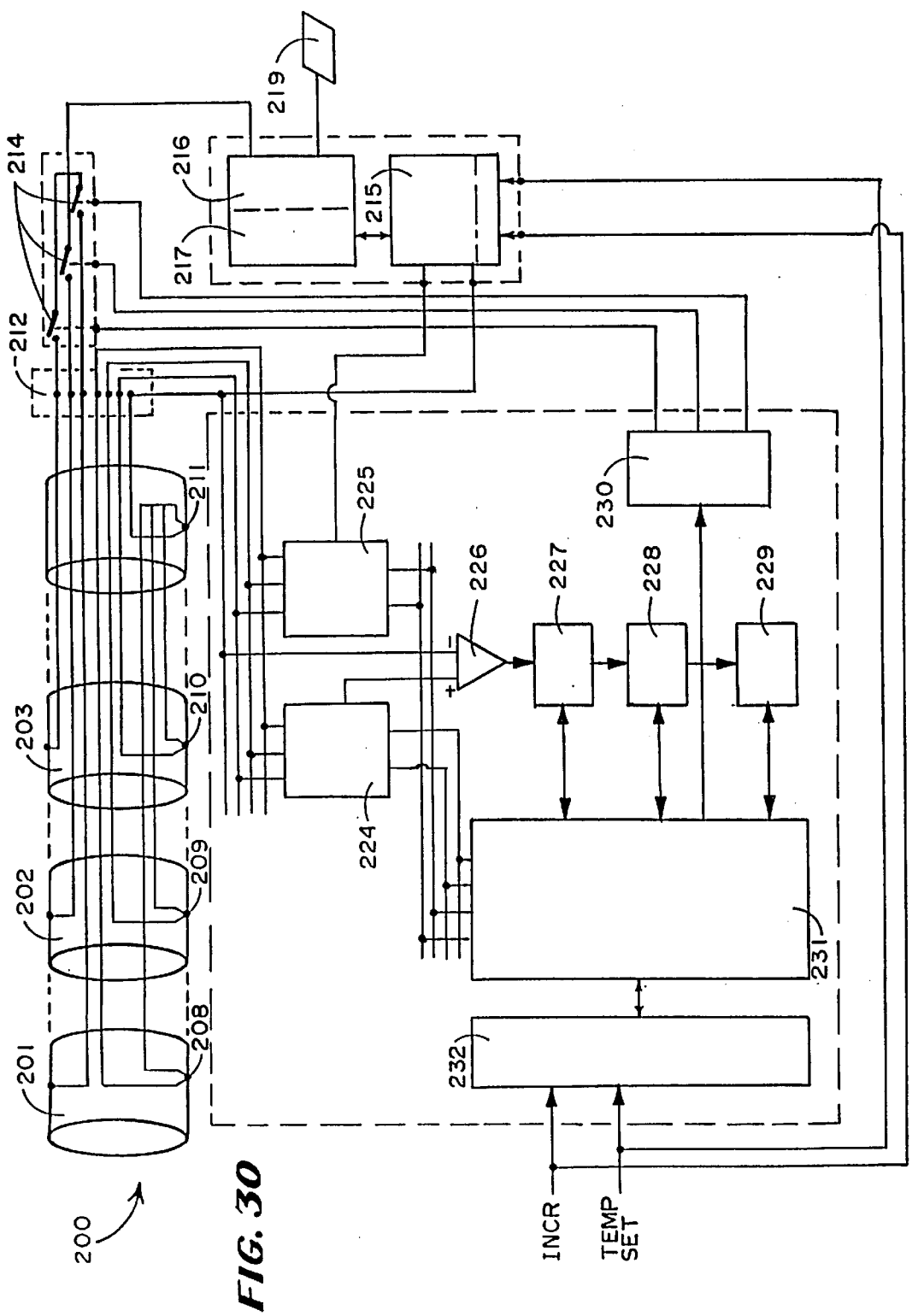
FIGS. 30 and 31 are schematic views of a system for controlling the application of ablating energy to multiple electrodes using multiple temperature sensing inputs.

In FIG. 30, the multiple sensing elements 80 comprise thermocouples 208, 209, and 210 individually associated with the multiple emitters of ablating energy, which comprise electrode regions 201, 202, and 203. The system 200 also includes a common reference thermocouple 211 carried within the coupler element 211 for exposure to the blood pool. Alternatively, other kinds of temperature sensing elements can be used, like, for example, thermistors, fluoroptic sensors, and resistive temperature sensors, in which case the reference sensor 211 would typically not be required.

The system 200 further includes an indifferent electrode 219 for operation in a uni-polar mode.

The ablating energy emitters 201, 202, 203 can comprise the rigid electrode segments 30 previously described. Alternatively, the electrode regions 201, 202, 203 can comprise a continuous or segmented flexible electrode of wrapped wire or ribbon. It should be appreciated that the system 200 can be used in association with any ablating element that employs multiple, independently actuated ablating elements.

The system 200 includes a source 217 of ablating energy. In FIG. 30, the source 217 generates radio frequency (RF) energy. The source 217 is connected (through a conventional isolated output stage 216) to an array of power switches 214, one for each electrode region 201, 202, and 203. A connector 212 (carried by the probe handle) electrically couples each electrode region 201, 203, 203 to its own power switch 214 and to other parts of the system 200.

The system 200 also includes a microcontroller 231 coupled via an interface 230 to each power switch 214. The microcontroller 231 turns a given power switch 214 on or off to deliver RF power from the source 217 individually to the electrode regions 201, 202, and 203. The delivered RF energy flows from the respective electrode region 201, 202, and 203, through tissue, to the indifferent electrode 219, which is connected to the return path of the isolated output stage 216.

Figure 31:
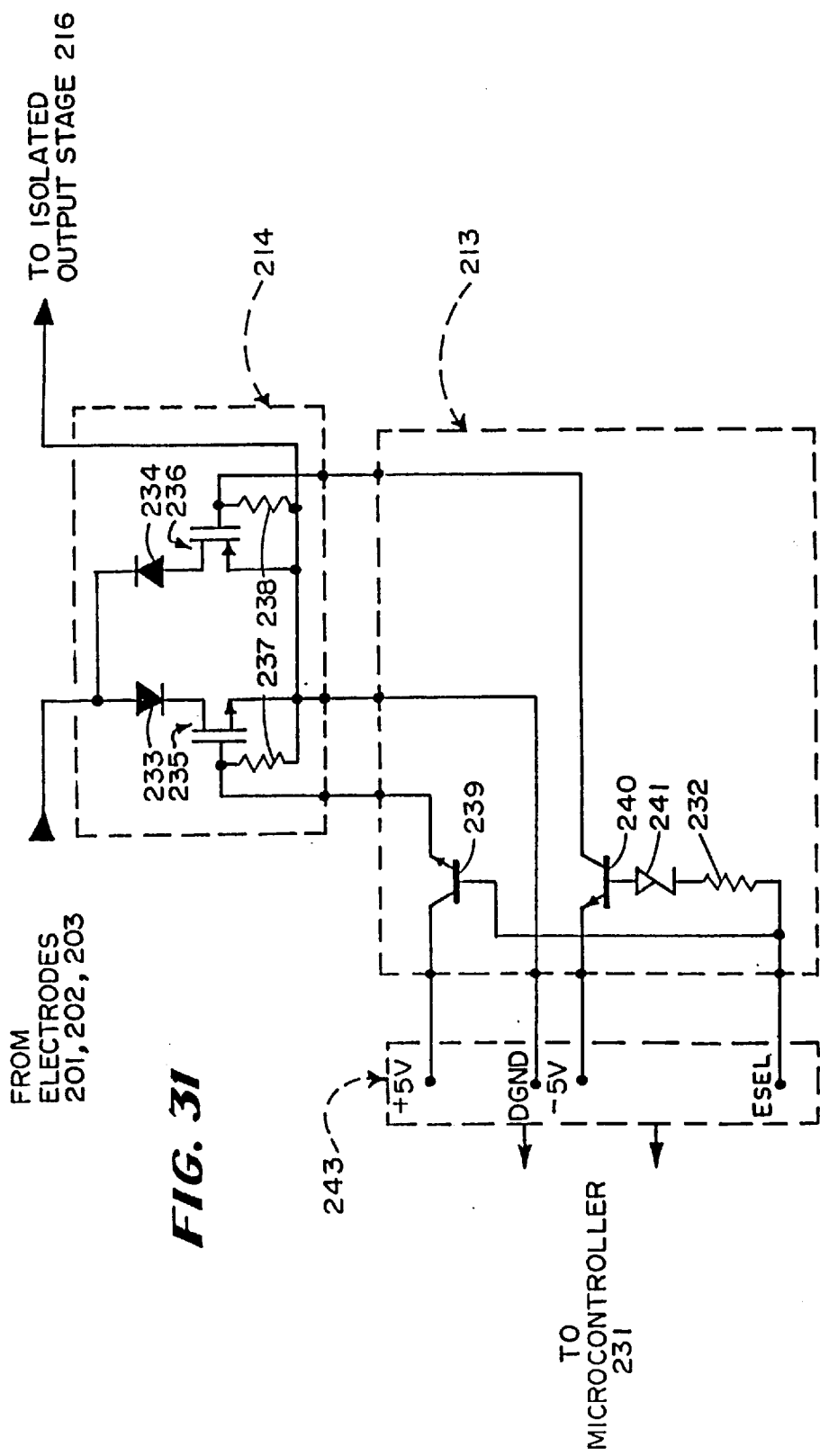

The power switch 214 and interface 230 configuration can vary according to the type of ablating energy being applied. FIG. 31 shows a representative implementation for applying RF ablating energy.

In this implementation, each power switch 214 includes an N-MOS power transistor 235 and a P-MOS power transistor 236 coupled in between the respective electrode region 201, 202, and 203 and the isolated output stage 216 of the power source 217.

A diode 233 conveys the positive phase of RF ablating energy to the electrode region. A diode 234 conveys the negative phase of the RF ablating energy to the electrode region. Resistors 237 and 238 bias the N-MOS and P-MOS power transistors 235 and 236 in conventional fashion.

The interface 230 for each power switch 214 includes two NPN transistors 239 and 240. The emitter of the NPN transistor 239 is coupled to the gate of the N-MOS power transistor 235. The collector of the NPN transistor 240 is coupled to the gate of the P-MOS power transistor 280.

The interface for each power switch 214 also includes a control bus 243 coupled to the microcontroller 231. The control bus 243 connects each power switch 214 to digital ground (DGND) of the microcontroller 231. The control bus 243 also includes a (+) power line (+5 V) connected to the collector of the NPN transistor 239 and a (−) power line (−5 V) connected to the emitter of the NPN interface transistor 240.

The control bus 243 for each power switch 214 further includes an $E_{SEL}$ line. The base of the NPN transistor 239 is coupled to the $E_{SEL}$ line of the control bus 243. The base of the NPN transistor 240 is also coupled the $E_{SEL}$ line of the control bus 243 via the Zener diode 241 and a resistor 232. $E_{SEL}$ line connects to the cathode of the Zener diode 241 through the resistor 232. The Zener diode 241 is selected so that the NPN transistor 240 turns on when $E_{SEL}$ exceeds about 3 volts (which, for the particular embodiment shown, is logic 1).

It should be appreciated that the interface 230 can be designed to handle other logic level standards. In the particular embodiment, it is designed to handle conventional TTL (transistor transfer logic) levels.

The microcontroller 231 sets $E_{SEL}$ of the control bus 243 either at logic 1 or at logic 0. At logic 1, the gate of the N-MOS transistor 235 is connected to (+) 5 volt line through the NPN transistors 239. Similarly, the gate of the P-MOS transistor 236 is connected to the (−) 5 volt line through the NPN transistor 240. This conditions the power transistors 235 and 236 to conduct RF voltage from the source 217 to the associated electrode region. The power switch 214 is "on."

When the microcontroller 231 sets $E_{SEL}$ at logic 0, no current flows through the NPN transistors 239 and 240. This conditions the power transistors 235 and 236 to block the conduction of RF voltage to the associated electrode region. The power switch 214 is "off."

The system 200 (see FIG. 30) further includes two analog multiplexers (MUX) 224 and 225. The multiplexers 224 and 225 receive voltage input from each thermocouple 208, 209, 210, and 211. The microcontroller 231 controls both multiplexers 224 and 225 to select voltage inputs from the multiple temperature sensing thermocouples 208, 209, 210, and 211.

The voltage inputs from the thermocouples 208, 209, 210, and 211 are sent to front end signal conditioning electronics. The inputs are amplified by differential amplifier 226, which reads the voltage differences between the copper wires of the thermocouples 208/209/210 and the reference thermocouple 211. The voltage differences are conditioned by element 227 and converted to digital codes by the analog-to-digital converter 228. The look-up table 229 converts the digital codes to temperature codes. The temperature codes are read by the microcontroller 231.

The microcontroller 231 compares the temperature codes for each thermocouple 208, 209, and 210 to preselected criteria to generate feedback signals. The preselected criteria are inputted through a user interface 232. These feedback signals control the interface power switches 214 via the interface 230, turning the electrodes 201, 202, and 203 off and on.

The other multiplexer 225 connects the thermocouples 208, 209, 210, and 211 selected by the microcontroller 231 to a temperature controller 215. The temperature controller 215 also includes front end signal conditioning electronics, as already described with reference to elements 226, 227, 228, and 229. These electronics convert the voltage differences between the copper wires of the thermocouples 208/209/210 and the reference thermocouple 211 to temperature codes. The temperature codes are read by the controller and compared to preselected criteria to generate feedback signals. These feedback signals control the amplitude of the voltage (or current) generated by the source 217 for delivery to the electrodes 201, 202, and 203.

Based upon the feedback signals of the microcontroller 231 and the temperature controller 215, the system 200 distributes power to the multiple electrode regions 201, 202, and 203 to establish and maintain a uniform distribution of temperatures along the ablating element. In this way, the system 200 obtains safe and efficacious lesion formation using multiple emitters of ablating energy.

The system 200 can control the delivery of ablating energy in different ways. Representative modes will now be described.

Individual Amplitudes/Collective Duty Cycle

The electrode regions 201, 202, and 203 will be symbolically designated E(J), where J represents a given electrode region (J=1 to N).

As before described, each electrode region E(J) has at least one temperature sensing element 208, 209, and 210, which will be designated S(J,K), where J represents the electrode region and K represents the number of temperature sensing elements on each electrode region (K=1 to M).

In this mode (see FIG. 32), the microcontroller 316 operates the power switch interface 230 to deliver RF power from the source 217 in multiple pulses of duty cycle 1/N.

With pulsed power delivery, the amount of power ($P_{E(J)}$) conveyed to each individual electrode region E(J) is expressed as follows:

$$P_{E(J)} \sim AMP_{E(J)}^2 \times DUTYCYCLE_{E(J)}$$

where:
$AMP_{E(J)}$ is the amplitude of the RF voltage conveyed to the electrode region E(J), and
$DUTYCYCLE_{E(J)}$ is the duty cycle of the pulse, expressed as follows:

$$DUTYCYCLE_{E(J)} = \frac{TON_{E(J)}}{TON_{E(J)} + TOFF_{E(J)}}$$

where:
$TON_{E(J)}$ is the time that the electrode region E(J) emits energy during each pulse period,
$TOFF_{E(J)}$ is the time that the electrode region E(J) does not emit energy during each pulse period.
The expression $TON_{E(J)} + TOFF_{E(J)}$ represents the period of the pulse for each electrode region E(J).

In this mode, the microcontroller 231 collectively establishes duty cycle ($DUTYCYCLE_{E(J)}$) of 1/N for each electrode region (N being equal to the number of electrode regions).

The microcontroller 231 may sequence successive power pulses to adjacent electrode regions so that the end of the duty cycle for the preceding pulse overlaps slightly with the beginning of the duty cycle for the next pulse. This overlap in pulse duty cycles assures that the source 217 applies power continuously, with no periods of interruption caused by open circuits during pulse switching between successive electrode regions.

In this mode, the temperature controller 215 makes individual adjustments to the amplitude of the RF voltage for each electrode region ($AMP_{E(J)}$), thereby individually changing the power $P_{E(J)}$ of ablating energy conveyed during the duty cycle to each electrode region, as controlled by the microcontroller 231.

In this mode, the microcontroller 231 cycles in successive data acquisition sample periods. During each sample period, the microcontroller 231 selects individual sensors S(J,K), and voltage differences are read by the controller 215 (through MUX 225) and converted to temperature codes TEMP(J).

When there is more than one sensing element associated with a given electrode region (for example, when edge-located sensing elements are used, as FIGS. 26 and 27 show), the controller 215 registers all sensed temperatures for the given electrode region and selects among these the highest sensed temperature, which constitutes TEMP(J).

In this mode, the controller 215 compares the temperature TEMP(J) locally sensed at each electrode E(J) during each data acquisition period to a set point temperature $TEMP_{SET}$ established by the physician. Based upon this comparison, the controller 215 varies the amplitude $AMP_{E(J)}$ of the RF voltage delivered to the electrode region E(J), while the microcontroller 231 maintains the $DUTYCYCLE_{E(J)}$ for that electrode region and all other electrode regions, to establish and maintain TEMP(J) at the set point temperature $TEMP_{SET}$.

The set point temperature $TEMP_{SET}$ can vary according to the judgment of the physician and empirical data. A representative set point temperature for cardiac ablation is believed to lie in the range of 40° C. to 95° C., with 70° C. being a representative preferred value.

The manner in which the controller 215 governs $AMP_{E(J)}$ can incorporate proportional control methods, proportional integral derivative (PID) control methods, or fuzzy logic control methods.

For example, using proportional control methods, if the temperature sensed by the first sensing element TEMP(1) >$TEMP_{SET}$, the control signal generated by the controller 215 individually reduces the amplitude $AMP_{E(1)}$ of the RF voltage applied to the first electrode region E(1), while the microcontroller 231 keeps the collective duty cycle $DUTYCYCLE_{E(1)}$ for the first electrode region E(1) the same. If the temperature sensed by the second sensing element TEMP(2)<$TEMP_{SET}$, the control signal of the controller 215 increases the amplitude $AMP_{E(2)}$ of the pulse applied to the second electrode region E(2), while the microcontroller 231 keeps the collective duty cycle $DUTYCYCLE_{E(2)}$ for the second electrode region E(2) the same as $DUTYCYCLE_{E(1)}$, and so on. If the temperature sensed by a given sensing element is at the set point temperature $TEMP_{SET}$, no change in RF voltage amplitude is made for the associated electrode region.

The controller 215 continuously processes voltage difference inputs during successive data acquisition periods to individually adjust $AMP_{E(J)}$ at each electrode region E(J), while the microcontroller 231 keeps the collective duty cycle the same for all electrode regions E(J). In this way, the mode maintains a desired uniformity of temperature along the length of the ablating element.

Using a proportional integral differential (PID) control technique, the controller 215 takes into account not only instantaneous changes that occur in a given sample period, but also changes that have occurred in previous sample periods and the rate at which these changes are varying over time. Thus, using a PID control technique, the controller 215 will respond differently to a given proportionally large instantaneous difference between TEMP (J) and $TEMP_{SET}$, depending upon whether the difference is getting larger or smaller, compared to previous instantaneous differences, and whether the rate at which the difference is changing since previous sample periods is increasing or decreasing.

Deriving Predicted Hottest Temperature

Because of the heat exchange between the tissue and the electrode region, the temperature sensing elements may not measure exactly the maximum temperature at the region. This is because the region of hottest temperature occurs beneath the surface of the tissue at a depth of about 0.5 to 2.0 mm from where the energy emitting electrode region (and the associated sensing element) contacts the tissue. If the power is applied to heat the tissue too quickly, the actual maximum tissue temperature in this subsurface region may exceed 100° C. and lead to tissue desiccation and/or micro-explosion.

Figure 33:
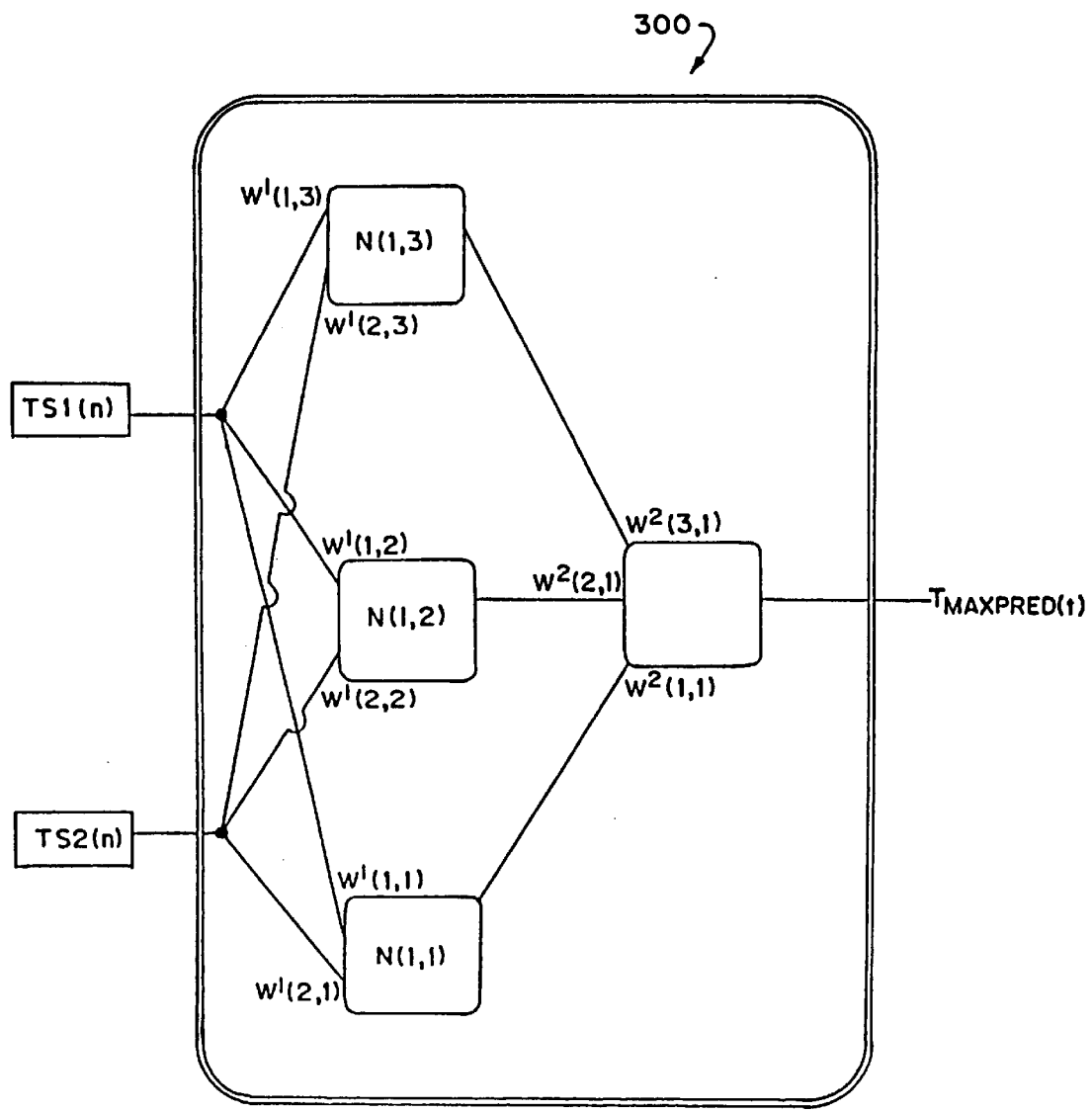
FIG. 33 is a schematic view of a neural network predictor, which receives as input the temperatures sensed by multiple sensing elements at a given electrode region and outputs a predicted temperature of the hottest tissue region.

FIG. 33 shows an implementation of a neural network predictor 300, which receives as input the temperatures sensed by multiple sensing elements S(J,K) at each electrode region, where J represents a given electrode region (J=1 to N) and K represents the number of temperature sensing elements on each electrode region (K=1 to M). The predictor 300 outputs a predicted temperature of the hottest tissue region $T_{MAXPRED}(t)$. The controller 215 and microcontroller 231 derive the amplitude and duty cycle control signals based upon $T_{MAXPRED}(t)$, in the same manners already described using TEMP (J).

Figure 32:
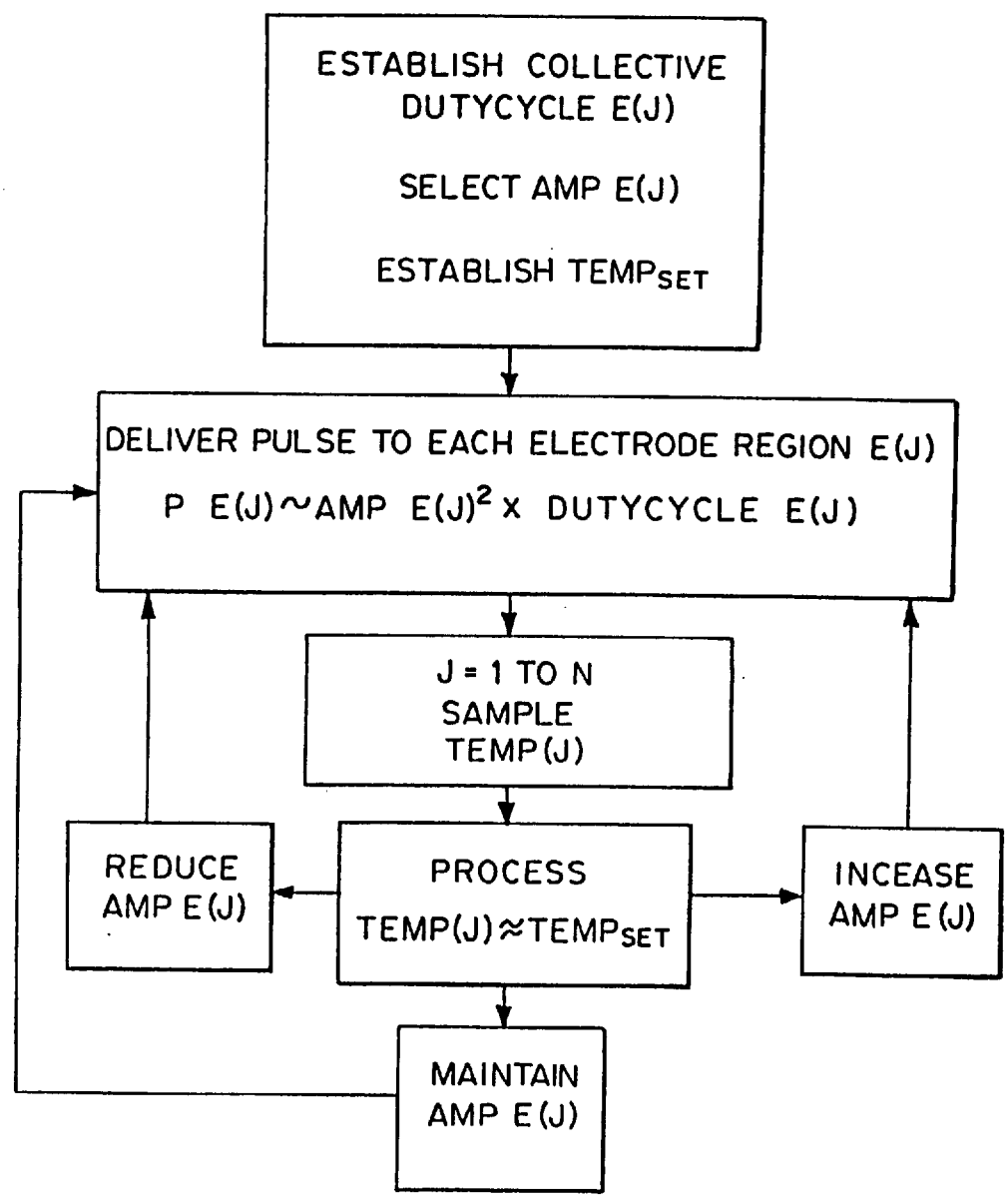
FIG. 32 is a schematic flow chart showing an implementation of the temperature feedback controller shown in FIGS. 30 and 31, using individual amplitude control with collective duty cycle control.

The predictor 300 uses a two-layer neural network, although more hidden layers could be used. As shown in FIG. 32, the predictor 300 includes a first and second hidden layers and four neurons, designated $N_{(L,X)}$, where L identifies the layer 1 or 2 and X identifies a neuron on that layer. The first layer (L=1) has three neurons (X=1 to 3), as follows $N_{(1,1)}$; $N_{(1,2)}$; and $N_{(1,3)}$. The second layer (L=2) comprising one output neuron (X=1), designated $N_{(2,1)}$.

Temperature readings from the multiple sensing elements, only two of which—TS1(n) and TS2(n)—are shown for purposes of illustration, are weighed and inputted to each neuron $N_{(1,1)}$; $N_{(1,2)}$; and $N_{(1,3)}$ of the first layer. FIG. 33 represents the weights as $W^L_{(k,N)}$, where L=1; k is the input sensor order; and N is the input neuron number 1, 2, or 3 of the first layer.

The output neuron $N_{(2,1)}$ of the second layer receives as inputs the weighted outputs of the neurons $N_{(1,1)}$; $N_{(1,2)}$; and $N_{(1,3)}$. FIG. 32 represents the output weights as $W^L_{(O,X)}$, where L=2; O is the output neuron 1, 2, or 3 of the first layer; and X is the input neuron number of the second layer. Based upon these weighted inputs, the output neuron $N_{(2,1)}$ predicts $T_{MAXPRED}(t)$. Alternatively, a sequence of past reading samples from each sensor could be used as input. By doing this, a history term would contribute to the prediction of the hottest tissue temperature.

The predictor 300 must be trained on a known set of data containing the temperature of the sensing elements TS1 and TS2 and the temperature of the hottest region, which have been previously acquired experimentally. For example, using a back-propagation model, the predictor 300 can be trained to predict the known hottest temperature of the data set with the least mean square error. Once the training phase is completed, the predictor 300 can be used to predict $T_{MAXPRED}(t)$.

Other types of data processing techniques can be used to derive $T_{MAXPRED}(t)$. See, e.g., copending patent application Ser. No. 08/266,934, filed Jun. 27, 1994, and entitled "Tissue Heating and Ablation Systems and Methods Using Predicted Temperature for Monitoring and Control."

The illustrated and preferred embodiments use digital processing controlled by a computer to analyze information and generate feedback signals. It should be appreciated that other logic control circuits using micro-switches, AND/OR gates, invertors, analog circuits, and the like are equivalent to the micro-processor controlled techniques shown in the preferred embodiments.

Various features of the invention are set forth in the following claims.

We claim:

1. A device for ablating body tissue comprising
a support element made of a material that does not conduct tissue ablation energy,
an electrode carried by the support element for contact with tissue, the electrode being made of a material that transmits ablation energy, the electrode having at least one longitudinal end edge that contacts the material of the support element, and
at least one temperature sensing element carried by and in thermal contact with the electrode and substantially abutting the at least one longitudinal end edge.

2. A device according to claim 1 and further including at least one additional temperature sensing element carried by the electrode away from the at least one edge.

3. A device for ablating body tissue comprising
a support element made of a material that does not conduct tissue ablation energy,
an electrode carried by the support element for contact with tissue, the electrode being made of a material that transmits ablation energy, the electrode having opposed longitudinal end edges that contact the material of the support element, and
temperature sensing elements carried by and in thermal contact with the electrode and substantially abutting the opposed longitudinal end edges.

4. A device according to claim 3 and further including at least one additional temperature sensing element carried by the electrode away from the opposed edges.

5. A device according to claim 1 or 2 or 3 or 4
wherein the electrode comprises a metallic material attached about the support element.

6. A device according to claim 1 or 2 or 3 or 4
wherein the electrode comprises wire wrapped about the support element.

7. A device according to claim 1 or 2 or 3 or 4
wherein the support element is flexible and includes means for flexing the support element.

8. A device according to claim 7
wherein the electrode is flexible and flexes with the support element.

9. A device according to claim 1 or 2 or 3 or 4
wherein the temperature sensing element comprises a thermistor.

10. A device according to claim 1 or 2 or 3 or 4
wherein the temperature sensing element comprises a thermocouple.

11. A device according to claim 1 or 2 or 3 or 4
and further including at least one additional temperature sensing element carried by the support body.

12. A device according to claim 1 or 2 or 3 or 4
wherein the electrode defines an inside and an outside and the temperature sensing element is carried inside the electrode.

13. A device according to claim 1 or 2 or 3 or 4
wherein the electrode defines an inside and an outside and the temperature sensing element is carried outside the electrode.

14. A device for ablating body tissue comprising
a support element made of a material that does not conduct tissue ablation energy,
an array of spaced apart electrodes carried by the support element for contact with tissue, each electrode being made of a material that transmits ablation energy, each electrode having opposed longitudinal end edges that contact the material of the support element, and
at least one temperature sensing element carried by and in thermal contact with one of the electrodes and substantially abutting at least one of its opposed longitudinal end edges.

15. A device according to claim 14
wherein each electrode carries at least one temperature sensing element adjacent to at least one of its opposed edges.

16. A device according to claim 14
wherein the array of electrodes includes a first electrode that begins the array and a second electrode that ends the array, and
wherein both the first and second electrodes carry at least one temperature sensing element adjacent to at least one of its edges.

17. A device according to claim 16
wherein the array of electrodes includes at least one intermediate electrode between the first and second electrodes.

18. A device according to claim 17
wherein the at least one intermediate electrode carries at least one temperature sensing element adjacent to at least one of its edges.

19. A device according to claim 17
wherein the at least one intermediate electrode carries at least one temperature sensing element.

20. A device according to claim 14
wherein the support body carries at least one temperature sensing element.

21. A device according to claim 14
wherein the at least one electrode comprises a metallic material attached about the support element.

22. A device according to claim 14
wherein the at least one electrode comprises wire wrapped about the support element.

23. A device according to claim 14
wherein the support element is flexible and includes means for flexing the support element.

24. A device according to claim 21
wherein the array of electrodes is flexible and flexes with the support element.

25. A device according to claim 14
wherein the temperature sensing element comprises a thermistor.

26. A device according to claim 14
wherein the temperature sensing element comprises a thermocouple.

27. A system for ablating body tissue comprising
a generator for supplying ablation energy,
a support element made of a material that does not conduct ablation energy,
an electrode operably connected to the generator and carried by the support element for contact with tissue, the electrode being made of a material that transmits ablation energy, the electrode having at least one longitudinal end edge that contacts the material of the support element, at least one temperature sensing element carried by and in thermal contact with the electrode and substantially abutting the at least one longitudinal end edge, and a controller coupled to the temperature sensing element and the generator to control the supply of ablation energy based, at least in part, upon temperature sensed by the at least one temperature sensing element.

28. A system for ablating body tissue comprising a generator for supplying ablation energy, a support element made of a material that does not conduct ablation energy, an electrode operably connected to the generator and carried by the support element for contact with tissue, the electrode being made of a material that transmits ablation energy, the electrode having opposed longitudinal end edges that contact the material of the support element, temperature sensing elements carried by and in thermal contact with the electrode and substantially abutting the opposed longitudinal end edges, and a controller coupled to the temperature sensing elements and the generator to control the supply of ablation energy based, at least in part, upon temperatures sensed by the temperature sensing elements.

29. A system for ablating body tissue comprising a generator for supplying ablation energy, a support element made of a material that does not conduct ablation energy, an electrode operably connected to the generator and carried by the support element for contact with tissue, the electrode being made of a material that transmits ablation energy, the electrode having opposed longitudinal end edges that contact the material of the support element, temperature sensing elements carried by the electrode the opposed longitudinal end edges, and a controller coupled to the temperature sensing elements and the generator to control the supply of ablation energy based, at least in part, upon temperatures sensed by the temperature sensing elements, wherein the controller includes means for selecting a temperature sensed by one of the temperature sensing elements that is higher than a temperature sensed by the other temperature sensing element and for controlling the supply of ablation energy based, at least in part, upon the selected temperature.

30. A system for ablating body tissue comprising a generator for supplying ablation energy, a support element made of a material that does not conduct ablation energy, an array of spaced apart electrodes operably connected to the generator and carried by the support element for contact with tissue, each electrode being made of a material that transmits ablation energy, each electrode having opposed longitudinal end edges that contact the material of the support element, the array including a first electrode that begins the array and a second electrode that ends the array, first and second temperature sensing elements carried by and in thermal contact with, respectively, the first and second electrodes and substantially abutting one of their respective opposed longitudinal end edges, and a controller coupled to the first and second temperature sensing elements and the generator to control the supply of ablation energy to the array of electrodes based, at least in part, upon temperatures sensed by the first and second temperature sensing elements.

31. A method for ablating body tissue comprising the steps of supplying ablation energy to an electrode carried by a support element made of a material that does not conduct ablation energy, the electrode having at least one longitudinal end edge that contacts the material of the support element, sensing temperature with at least one temperature sensing element carried by and in thermal contact with the electrode and substantially abutting the at least one longitudinal end edge, and controlling the supply of ablation energy based, at least in part, upon temperature sensed by the at least one temperature sensing element.

32. A method for ablating body tissue comprising the steps of supplying ablation energy to an electrode carried by a support element made of a material that does not conduct ablation energy, the electrode having opposed longitudinal end edges that contact the material of the support element, sensing temperatures with temperature sensing elements carried by and in thermal contact with the electrode and substantially abutting the opposed longitudinal end edges, and controlling the supply of ablation energy based, at least in part, upon temperatures sensed by the temperature sensing elements.

33. A method according to claim 32 wherein, in controlling the supply of ablation energy, a temperature sensed by one of the temperature sensing elements is selected that is higher than a temperature sensed by the other temperature sensing element and the supply of ablation energy is controlled based, at least in part, upon the selected temperature.

34. A method for ablating body tissue comprising the steps of supplying ablation energy to an array of spaced apart electrodes carried by a support element made of a material that does not conduct ablation energy, each electrode in the array having opposed longitudinal end edges that contact the material of the support element, the array including a first electrode that begins the array and a second electrode that ends the array, sensing temperatures with first and second temperature sensing elements carried by and in thermal contact with, respectively, the first and second electrodes and substantially abutting one of their respective opposed longitudinal end edges, and controlling the supply of ablation energy to the array of electrodes based, at least in part, upon temperatures sensed by the first and second temperature sensing elements.

35. A device for ablating body tissue, comprising:

a support element defining a length made of material that does not conduct tissue ablation energy;

an electrode carried by the support element for contact with tissue made of material that transmits ablation energy, the electrode defining first and second longitudinal end edges, an interior surface, an exterior surface and a length from the first longitudinal end edge to the second longitudinal end edge that is substantially less than the length of the support element, the first and second longitudinal end edges being in contact with the material that does not conduct tissue ablation energy; and a temperature sensing element carried by and in thermal contact with the electrode, the temperature sensing element being located on one of the interior surface and the exterior surface of the electrode and substantially closer to the first longitudinal end edge than to the second longitudinal end edge.

36. A device as claimed in claim 35, wherein the temperature sensing element substantially abuts the first longitudinal edge of the electrode.

37. A device as claimed in claim 35, wherein the support element defines a distal tip and the electrode is in spaced relation to the distal tip of the support element.

38. A device as claimed in claim 35, wherein the temperature sensing element defines a first temperature sensing element, the device further comprising:

a second temperature sensing element carried by the electrode.

39. A device as claimed in claim 38, wherein the first temperature sensing element substantially abuts the first longitudinal edge of the electrode and the second temperature sensing element substantially abuts the second longitudinal edge of the electrode.

40. A device as claimed in claim 35, wherein the electrode comprises an array of electrodes including first and second electrodes defining longitudinal ends of the array, and the first and second electrodes include respective temperature sensing elements.

41. A device as claimed in claim 40, wherein the array includes a third electrode located between the first and second electrodes, and the third electrode includes a temperature sensing element.

42. A device for ablating body tissue, comprising:

a support element made of material that does not conduct tissue ablation energy;

an electrode carried by the support element for contact with tissue made of material that transmits ablation energy, the electrode defining first and second longitudinal edges, an interior surface and an exterior surface, the first and second longitudinal end edges being in contact with the material that does not conduct tissue ablation energy; and a temperature sensing element carried by and in thermal contact with the electrode, the temperature sensing element being located on the exterior surface of the electrode and substantially abutting the first longitudinal end edge.

43. A device as claimed in claim 42, wherein the support element defines a distal tip and the electrode is in spaced relation to the distal tip of the support element.

44. A device as claimed in claim 42, wherein the temperature sensing element defines a first temperature sensing element, the device further comprising:

a second temperature sensing element carried by the electrode.

45. A device as claimed in claim 44, wherein the second temperature sensing element substantially abuts the second longitudinal end edge of the electrode.

46. A device as claimed in claim 42, wherein the electrode comprises an array of electrodes including first and second electrodes defining the longitudinal ends of the array, and the first and second electrodes include respective temperature sensing elements.

47. A device as claimed in claim 46, wherein the array includes a third electrode located between the first and second electrodes, and the third electrode includes a temperature sensing element.

48. A device for ablating body tissue, comprising:

a support element made of material that does not conduct tissue ablation energy;

an electrode carried by the support element for contact with tissue made of material that transmits ablation energy, the electrode defining first and second longitudinal end edges, an interior surface and an exterior surface, the first and second longitudinal end edges being in contact with the material that does not conduct tissue ablation energy; and temperature sensing means for sensing the temperature of the first longitudinal end edge of the electrode.

49. A device as claimed in claim 48, wherein the temperature sensing means defines first temperature sensing means, the device further comprising:

second temperature sensing means for sensing the temperature of the second longitudinal end edge of the electrode.

50. A device as claimed in claim 48, wherein the temperature sensing means is associated with the outer surface of the electrode.

* * * * *